(12) United States Patent
Capdevila Urbaneja et al.

(10) Patent No.: US 10,800,748 B2
(45) Date of Patent: Oct. 13, 2020

(54) PROCESS FOR THE MANUFACTURE OF R-6-HYDROXY-8-[1-HYDROXY-2-[2-(4-METHOXYPHENYL)-1,1-DIMETHYLETHYLAMINOETHYL]-2H-1,4-BENZOXAZIN-3(4H)-ONE HYDROCHLORIDE

(71) Applicant: INKE, S.A., Barcelona (ES)

(72) Inventors: Enric Capdevila Urbaneja, Barcelona (ES); Juan Huguet Clotet, Barcelona (ES); Pere Dalmases Barjoan, Barcelona (ES)

(73) Assignee: INKE, S.A., Castellbisbal-Barcelona (ES)

( * ) Notice: Subject to any disclaimer, the term of this patent is extended or adjusted under 35 U.S.C. 154(b) by 0 days.

(21) Appl. No.: 16/465,762

(22) PCT Filed: Dec. 19, 2017

(86) PCT No.: PCT/EP2017/083444
§ 371 (c)(1),
(2) Date: May 31, 2019

(87) PCT Pub. No.: WO2018/114887
PCT Pub. Date: Jun. 28, 2018

(65) Prior Publication Data
US 2020/0062723 A1    Feb. 27, 2020

(30) Foreign Application Priority Data

Dec. 20, 2016  (EP) .................................... 16382628
Jul. 10, 2017  (EP) .................................... 17382449

(51) Int. Cl.
*C07D 265/36*    (2006.01)

(52) U.S. Cl.
CPC ........ *C07D 265/36* (2013.01); *C07B 2200/13* (2013.01)

(58) Field of Classification Search
CPC .................................................. C07D 265/36
USPC ........................................................ 544/105
See application file for complete search history.

(56) References Cited

FOREIGN PATENT DOCUMENTS

| WO | WO2004045618 A2 | 6/2004 |
| WO | WO2007020227 A1 | 2/2007 |
| WO | WO2008090193 A2 | 7/2008 |
| WO | WO2010111005 A2 | 9/2010 |

OTHER PUBLICATIONS

Armarego, W., et al., "Chemical Methods Used in Purification", "Purification of Laboratory Chemicals", 2013, pp. Chapter 2: 76, Publisher: Elsevier.

*Primary Examiner* — Kahsay Habte
(74) *Attorney, Agent, or Firm* — Hultquist, PLLC; Steven J. Hultquist

(57) ABSTRACT

The present invention provides an improved process for the manufacture (R)-6-hydroxy-8-[1-hydroxy-2-[2-(4-methoxyphenyl)-1,1-dimethyl-ethylamino-ethyl]-2H-1,4-benzoxazin-3(4H)-one, in high purity and high yield, through the use of 1,1-dimethyl-2-(4-methoxyphenyl)ethyl amine L-tartrate salt, 1,1-dimethyl-2-(4-methoxyphenyl) ethyl amine maletate salt or the camphorsulfonate salt of intermediate (4). The invention also relates to said salts, to processes for preparing them and to their use for the manufacture of (R)-6-hydroxy-8-[1-hydroxy-2-[2-(4-methoxyphenyl)-1,1-dimethyl-ethylamino-ethyl]-2H-1,4-benzoxazin-3(4H)-one or a pharmaceutically acceptable salt thereof.

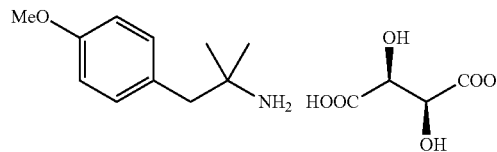

(3)·L-tartaric acid

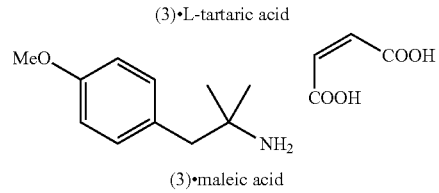

(3)·maleic acid

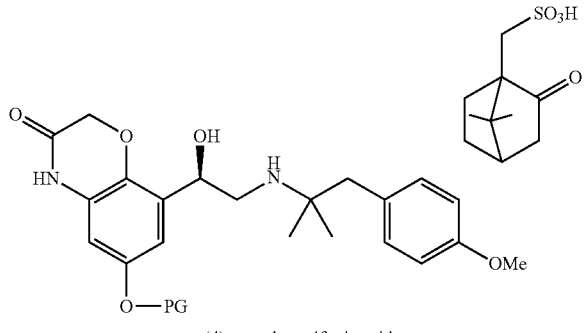

(4)·camphorsulfonic acid

16 Claims, 4 Drawing Sheets

PROCESS FOR THE MANUFACTURE OF R-6-HYDROXY-8-[1-HYDROXY-2-[2-(4-METHOXYPHENYL)-1,1-DIMETHYLETHYLAMINOETHYL]-2H-1,4-BENZOXAZIN-3(4H)-ONE HYDROCHLORIDE

CROSS-REFERENCE TO RELATED APPLICATIONS

This application is a U.S. national phase under the provisions of 35 U.S.C. § 371 of International Patent Application No. PCT/EP17/83444 filed Dec. 19, 2017, which in turn claims priority of European Patent Application No. 16382628.2 filed Dec. 20, 2016 and European Patent Application No. 17382449.1 filed Jul. 10, 2017. The disclosures of International Patent Application No. PCT/EP17/83444, European Patent Application No. 16382628.2 and European Patent Application No. 17382449.1 are hereby incorporated herein by reference in their respective entireties, for all purposes.

FIELD OF THE INVENTION

The present invention provides an improved process for the manufacture of olodaterol or a pharmaceutically acceptable salt thereof, preferably the hydrochloride salt, in high chemical and enantiomeric purity and high yield, through the 1,1-dimethyl-2-(4-methoxyphenyl)ethyl amine L-tartrate salt, the 1,1-dimethyl-2-(4-methoxyphenyl)ethyl amine maleate salt and/or the camphorsulfonate salt of intermediate (4). The invention also relates to said salts, to a process for preparing them and to their use for the manufacture of olodaterol or a pharmaceutically acceptable salt thereof.

BACKGROUND OF THE INVENTION (R)-6-Hydroxy-8-[1-hydroxy-2-[2-(4-methoxyphenyl)-1,1-dimethylethylaminoethyl]-2H-1,4-benzoxazin-3(4H)-one, the compound of formula (1), also known as the R-enantiomer of olodaterol, is a long-acting $\beta_2$-adrenoreceptor agonist (LABA), commercialized as its hydrochloride salt under the brand name of Striverdi® Respimat®, for the once-daily treatment of chronic obstructive pulmonary disease (COPD).

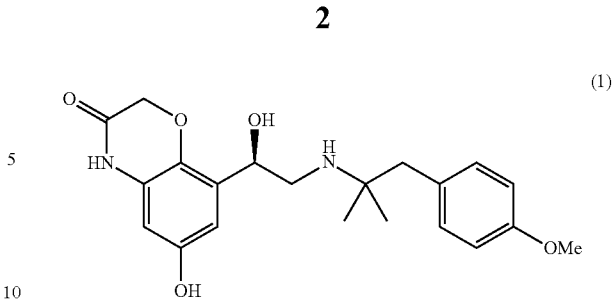

WO 2004/045618 A2 first discloses the preparation of racemic olodaterol via the reaction of a glyoxal hydrate intermediate with 1,1-dimethyl-2-(4-methoxyphenyl)ethyl amine in the presence of a hydride source. After hydrogenation, racemic olodaterol is recrystallized and the R-enantiomer is separated by chiral chromatography. This process is not feasible for industrial application since the preparation of the target R-enantiomer of olodaterol is carried out by means of chiral chromatographic methods, which are generally expensive, environmentally unfriendly and time consuming. In addition, the preparation and purity of 1,1-dimethyl-2-(4-methoxyphenyl)ethyl amine intermediate are not disclosed.

WO 2005/111005 A1 discloses the preparation of R-enantiomer of olodaterol hydrochloride, compound of formula (1).HCl, as shown in Scheme 1. Basically, (R)-6-benzyloxy-8-oxiranyl-4H-benzo[1,4]oxazin-3-one (2) is reacted with 1,1-dimethyl-2-(4-methoxyphenyl)ethyl amine in isopropanol under microwave irradiation at 135° C. to provide advanced intermediate (4), which is purified by column chromatography and further recrystallized. The R-enantiomer of olodaterol hydrochloride is obtained after hydrogenation and further reaction with hydrochloric acid. Advanced intermediate (4) is obtained in only 63% yield and purity is not disclosed. This process implies various drawbacks. Not only is the microwave radiation technique not easily feasible for industrial application, but also the purification of advanced intermediate (4) by chromatographic methods. Moreover, the preparation and purity of 1,1-dimethyl-2-(4-methoxyphenyl)ethyl amine are not disclosed.

Scheme 1

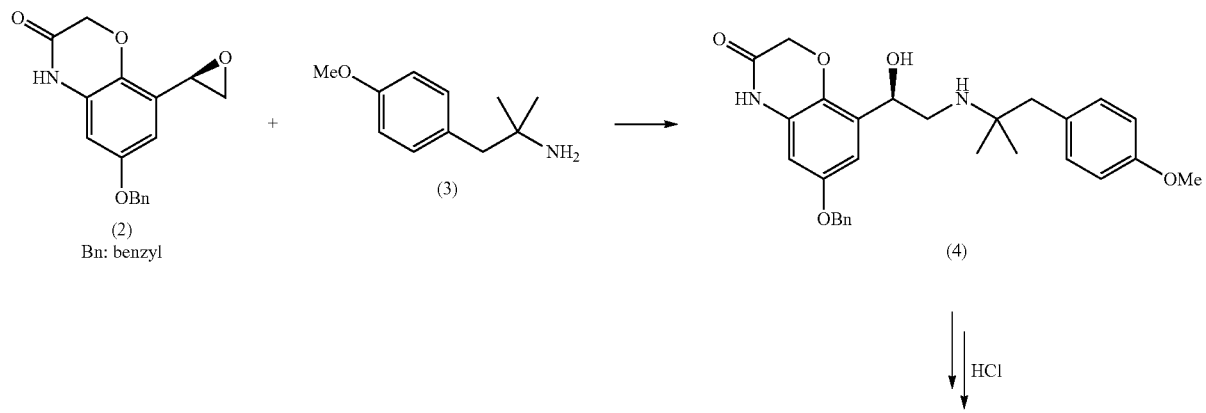

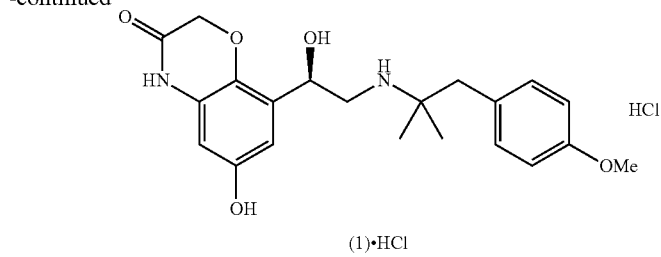

WO 2007/020227 A1 discloses the preparation of R-enantiomer of olodaterol hydrochloride as shown in Scheme 2. In particular, (R)-6-benzyloxy-8-oxiranyl-4H-benzo[1,4]oxazin-3-one (2) is reacted with 1,1-dimethyl-2-(4-methoxyphenyl)ethyl amine (3) in 1,4-dioxane at 97° C., and then, treated with hydrochloric acid to provide the hydrochloride salt of advanced intermediate (4), which is further hydrogenated. Intermediate (4).HCl is obtained in 89.5-99.5% purity.

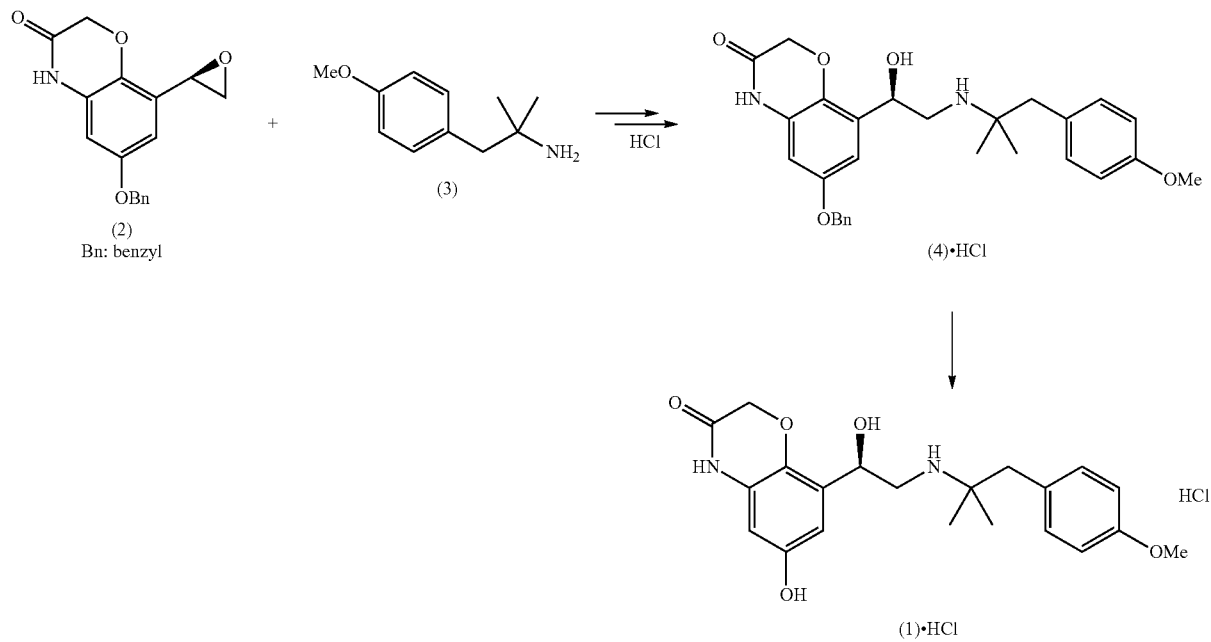

WO 2007/020227 A1 also discloses the preparation of 1,1-dimethyl-2-(4-methoxyphenyl)ethyl amine (3) from 4-methoxyphenylacetone (5), in three reaction steps as shown is Scheme 3, in 94-96% purity (HPLC method) in an overall yield of 34-43% (as calculated from the examples data provided in WO 2007/020227 A1).

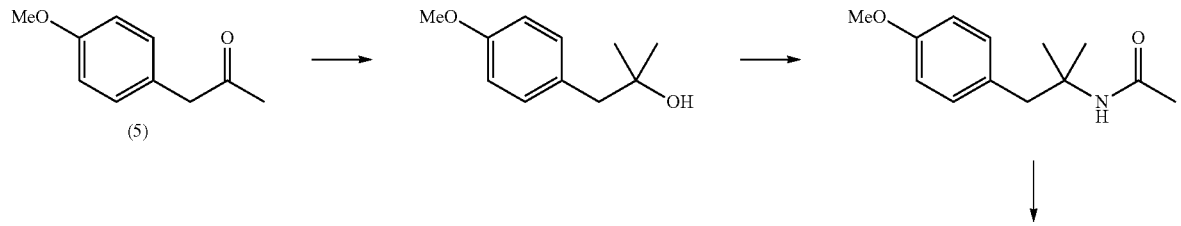

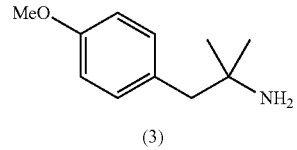

(3)

WO 2008/090193 A2 discloses the preparation of R-enantiomer of olodaterol hydrochloride as shown Scheme 4. (R)-6-benzyloxy-8-oxiranyl-4H-benzo[1,4]oxazin-3-one (2) is reacted with 1,1-dimethyl-2-(4-methoxyphenyl)ethyl amine (3) in toluene at reflux. Then, treatment with hydrochloric acid to provide intermediate (4).HCl in 95-99.5% purity, followed by a hydrogenation step provides the R-enantiomer of olodaterol hydrochloride. In addition, WO 2008/090193 A2 discloses the preparation of the hydrochloride salt of 1,1-dimethyl-2-(4-methoxyphenyl)ethyl amine from 4-methoxyphenylacetone, as in above Scheme 3, in >99.5% purity (HPLC method) in an overall yield of 41-54% (as calculated from the examples data provided in WO 2008/090193 A2).

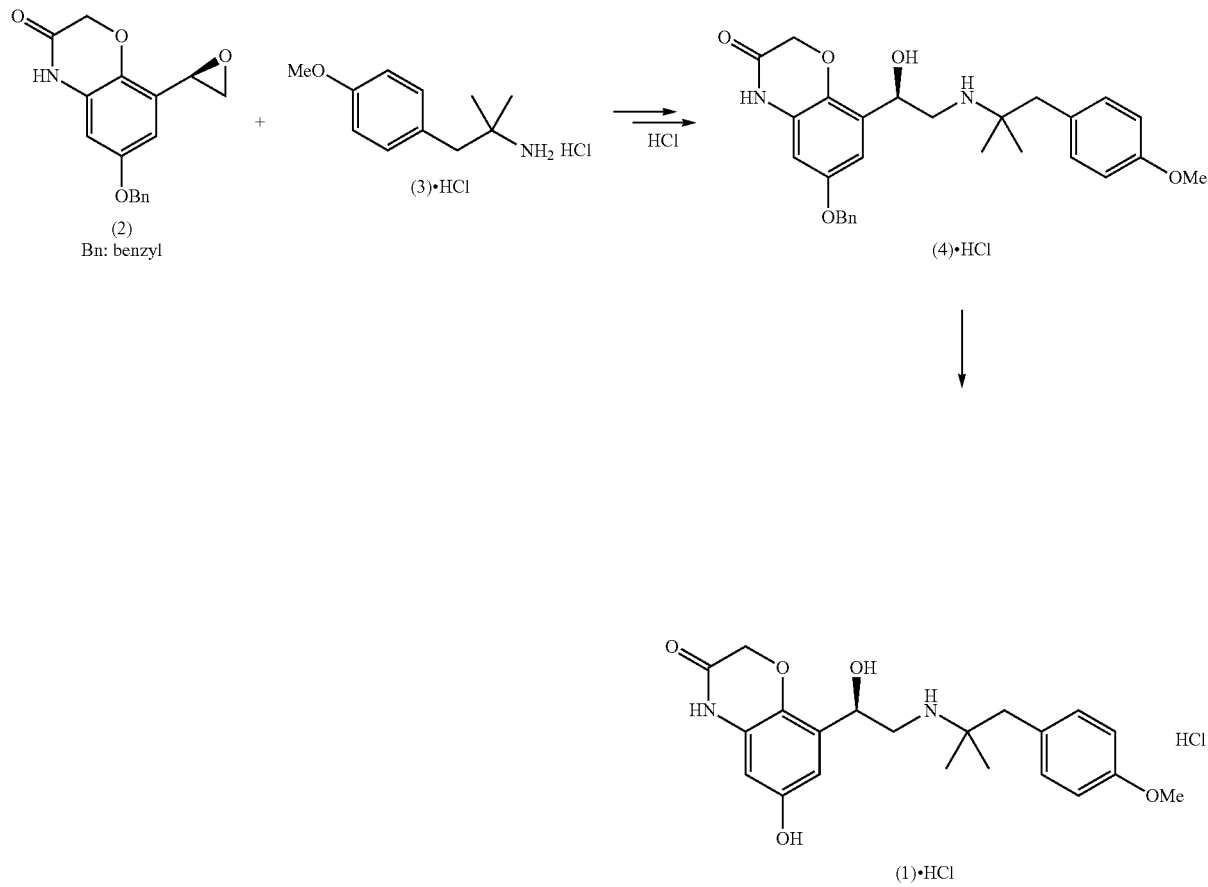

Scheme 4

The above prior art documents WO 2007/020227 A1 and WO 2008/090193 A2 disclose the preparation of 1,1-dimethyl-2-(4-methoxyphenyl)ethyl amine intermediate, either as a base or as its hydrochloride salt, in low yields, which implies the increase of the cost of the final olodaterol process and the pharmaceutical compositions containing it, which already resulted in expensive medications.

Known process for preparing amines as key intermediates in the synthesis of new β-sympathomimetic compounds (olodaterol is not disclosed) is described in the article Archiv der Pharmazie (Weinheim, Germany), 1983, 316(3), pages 193-2011. Particularly, the 1,1-dimethyl-2-(4-methoxyphenyl)ethyl amine hydrochloride is prepared, as shown in Scheme 5, in an overall yield of 66% from 4-(2-methyl-2-nitropropyl)phenol in three synthetic steps. 4-(2-methyl-2-nitropropyl)phenol, compound of formula (6), is methylated to give the nitro intermediate (7), which is further recrystallized. Then, the nitro group is reduced by hydrogenation and the obtained amine is treated with hydrochloric acid to provide 1,1-dimethyl-2-(4-methoxyphenyl)ethyl amine hydrochloride. Purity is not disclosed.

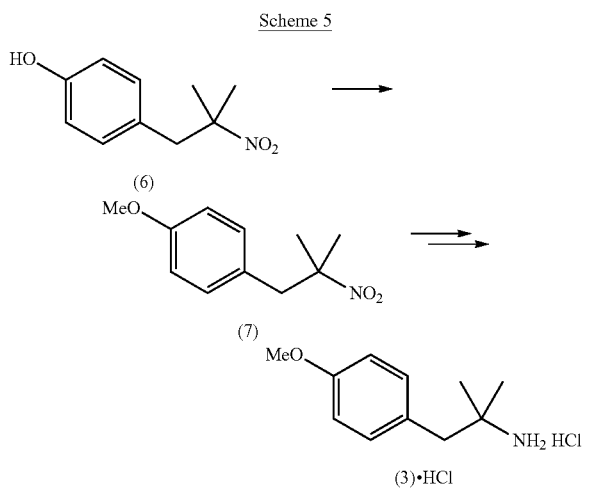

Scheme 5

Therefore, there is a need in developing feasible methods for the manufacture of olodaterol or a pharmaceutically acceptable salt thereof, preferably the R-enantiomer of olodaterol hydrochloride, in high purity and high yield.

BRIEF DESCRIPTION OF THE INVENTION

The inventors have unexpectedly found that purifying intermediate (4), used in the process of preparation of olodaterol, by formation of the camphorsulfonate salt, in particular the (R)-(−)-camphorsulfonate salt, provides an increase in the chemical and enantiomeric purity of final olodaterol or salt thereof, preferably the R-enantiomer of olodaterol hydrochloride.

The present inventors have also surprisingly found 1,1-dimethyl-2-(4-methoxyphenyl)ethyl amine L-tartrate salt useful for preparing olodaterol or pharmaceutically acceptable salt thereof, preferably the R-enantiomer of olodaterol hydrochloride, in high chemical and enantiomeric purity and high yield. Particularly, the 1,1-dimethyl-2-(4-methoxyphenyl)ethyl amine L-tartrate salt is prepared in high purity and high yield in a robust and reproducible manner. In addition, the 1,1-dimethyl-2-(4-methoxyphenyl)ethyl amine L-tartrate salt is not hygroscopic as compared to the prior art hydrochloride salt.

In addition, the inventors have surprisingly found that the 1,1-dimethyl-2-(4-methoxyphenyl)ethyl amine maleate salt is useful for reducing or even eliminating impurities in the process for preparing olodaterol or a pharmaceutically acceptable salt thereof, preferably the R-enantiomer of olodaterol hydrochloride.

Thus, a first aspect of the present invention provides the camphorsulfonate salt of intermediate (4), wherein PG is a hydroxyl protecting group and to solid forms thereof.

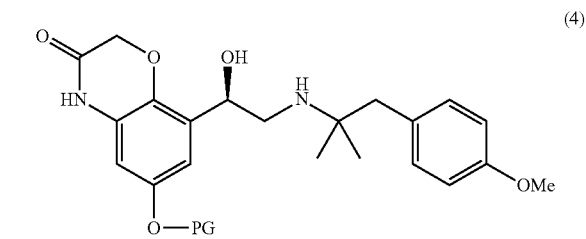

A second aspect of the present invention provides a process for preparing the camphorsulfonate salt of intermediate (4) as defined in the first aspect.

A third aspect of the present invention relates to a process for the manufacture of olodaterol, preferably the R-enantiomer of olodaterol hydrochloride, which makes use of the camphorsulfonate salt of intermediate (4) as defined in the first aspect.

A fourth aspect of the present invention provides 1,1-dimethyl-2-(4-methoxyphenyl)ethyl amine L-tartrate salt, wherein the molar ratio of 1,1-dimethyl-2-(4-methoxyphenyl)ethyl amine to L-tartaric acid is 1:1 and to solid forms thereof.

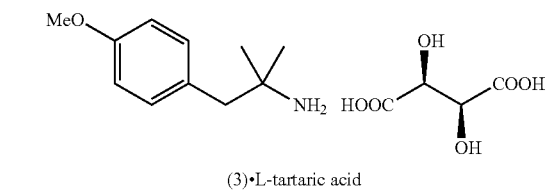

(3)·L-tartaric acid

A fifth aspect of the present invention provides a process for preparing 1,1-dimethyl-2-(4-methoxyphenyl)ethyl amine L-tartrate salt as defined in the fourth aspect.

A sixth aspect of the present invention provides 1,1-dimethyl-2-(4-methoxyphenyl)ethyl amine maleate salt and to solid forms thereof.

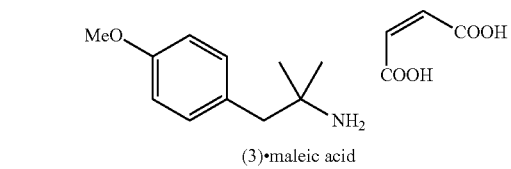

(3)·maleic acid

A seventh aspect of the present invention provides a process for preparing 1,1-dimethyl-2-(4-methoxyphenyl) ethyl amine maleate salt as defined in the sixth aspect.

Further aspects of the present invention relate to the use of the camphorsulfonate salt of intermediate (4) as defined in the first and second aspects, the use of 1,1-dimethyl-2-

(4-methoxyphenyl)ethyl amine L-tartrate salt according to the fourth and fifth aspects and to the use of 1,1-dimethyl-2-(4-methoxyphenyl)ethyl amine maleate salt as defined in the sixth and seventh aspects for preparing olodaterol or a pharmaceutically acceptable salt thereof, preferably the R-enantiomer of olodaterol hydrochloride.

BRIEF DESCRIPTION OF THE DRAWINGS

Examples of the invention are illustrated with the following drawings.

DEFINITIONS

Figure 1:
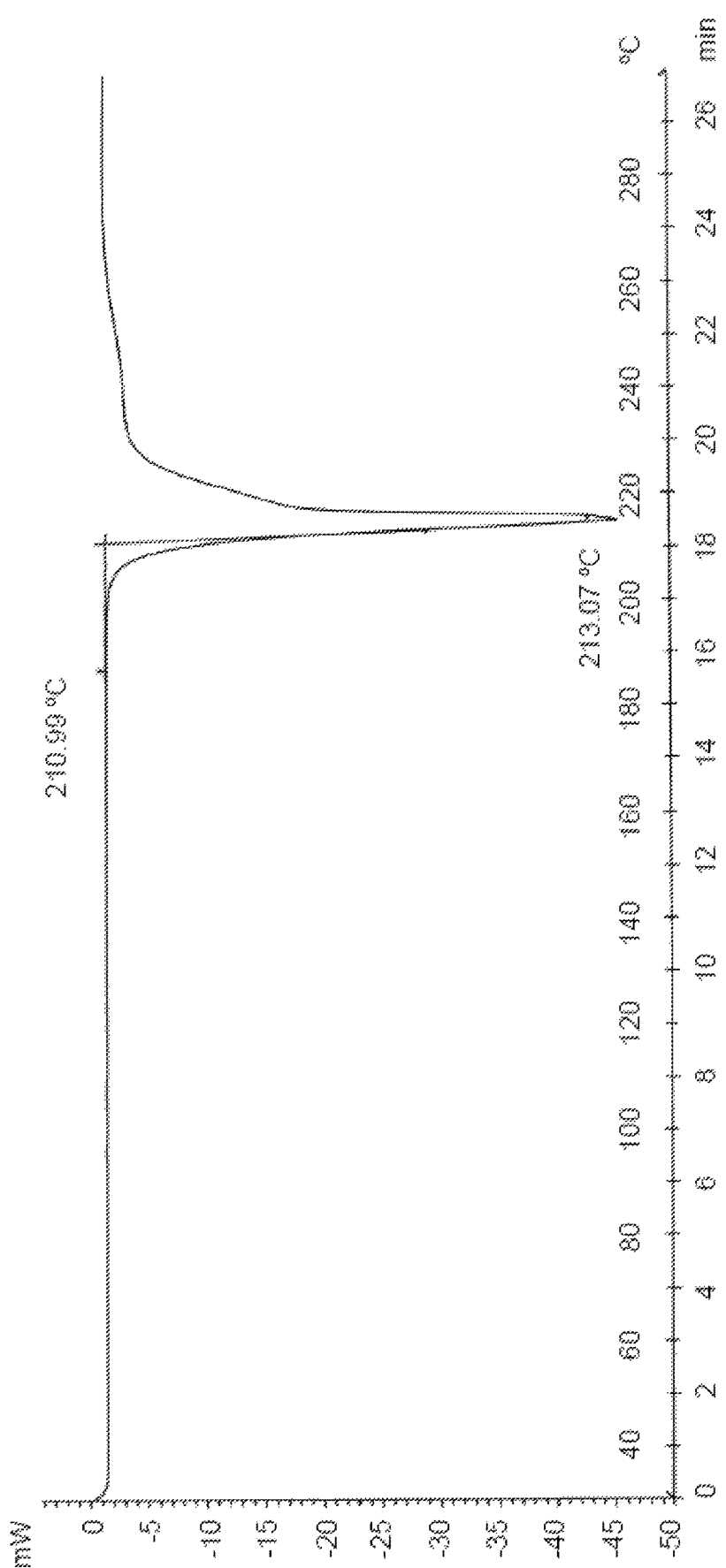
FIG. 1 shows the DSC analysis of 1,1-dimethyl-2-(4-methoxyphenyl)ethyl amine L-tartrate salt prepared as in example 2.

When describing the compounds and methods of the invention, the following terms have the following meanings, unless otherwise indicated.

The term "olodaterol" refers to 6-hydroxy-8-[1-hydroxy-2-[2-(4-methoxyphenyl)-1,1-dimethylethylaminoethyl]-2H-1,4-benzoxazin-3(4H)-one.

As used herein the term organic solvent refers to an organic molecule capable of dissolving another substance (i.e., the solute). Organic solvents may be liquids at room temperature. Examples of organic solvents that may be used for the present invention include, but are not limited to: hydrocarbon solvents (e.g., n-pentane, n-hexane, n-heptane, n-octane, cyclohexane, methylcyclohexane, decahydronaphthalene, etc.) which also includes aromatic hydrocarbon solvents (e.g., benzene, toluene, o-xylene, m-xylene, and p-xylene), halogenated hydrocarbon solvents (e.g., carbon tetrachloride, 1,2-dichloroethane, dichloromethane, chloroform, etc.), ester solvents (e.g., ethyl formate, methyl acetate, ethyl acetate, isopropyl acetate, butyl acetate, isobutyl acetate, ethyl malonate, etc.), ketone solvents (e.g., acetone, methyl ethyl ketone or 2-butanone, methyl isobutyl ketone, cyclohexanone, cyclopentanone, 3-pentanone, etc.), ether solvents (e.g., diethyl ether, dipropyl ether, diphenyl ether, isopropyl ether, tert-butyl methyl ether, tetrahydrofuran, 2-methyltetrahydrofuran, 1,4-dioxane, methyl phenyl ether or anisole, etc.), amine solvents (e.g., propyl amine, diethylamine, triethylamine, aniline, pyridine), alcohol solvents (e.g., methanol, ethanol, isopropanol, 1-propanol, 2-methyl-1-propanol, 1-butanol, 2-butanol, 1-pentanol, 3-methyl-1-butanol, tert-butanol, 1-octanol, benzyl alcohol, phenol, trifluoroethanol, glycerol, ethylene glycol, propylene glycol, m-cresol, etc.), acid solvents (e.g., acetic acid, hexanoic acid, etc.), nitrobenzene, N,N-dimethylformamide, N, N,-dimethylacetamide, dimethylsulfoxide, N-methyl-2-pyrrolidone, acetonitrile, propionitrile, butyronitrile, silicone solvents (e.g., silicone oils, polysiloxanes, cyclosilicones). In some embodiments, the organic solvent may be formed by the combination of two or more organic solvents.

The term polar solvent as used herein means a solvent having a dielectric constant of at least 3, said dielectric constant being the ratio of the electrical capacity of a capacitor filled with the solvent to the electrical capacity of the evacuated capacitor at 20-25° C. The values of dielectric constant of solvents are disclosed in Vogel's Textbook of Practical Organic Chemistry 5$^{th}$ Edition, Appendix 5. Examples of polar solvents are dichloromethane, tetrahydrofuran, ester solvents (e.g., ethyl formate, methyl acetate, ethyl acetate, ethyl malonate, etc.), ketone solvents (e.g., acetone, methyl ethyl ketone or 2-butanone, cyclohexanone, cyclopentanone, 3-pentanone, etc.), amine solvents (e.g., propyl amine, diethylamine, triethylamine, aniline, pyridine), alcohol solvents (e.g., methanol, ethanol, isopropanol, 1-propanol, 1-butanol, 1-octanol, benzyl alcohol, phenol, trifluoroethanol, glycerol, ethylene glycol, propylene glycol, m-cresol, etc.), acid solvents (e.g., acetic acid, hexanoic acid, etc.), nitrobenzene, N,N-dimethylformamide, N,N,-dimethylacetamide, dimethylsulfoxide, N-methyl-2-pyrrolidone, acetonitrile propionitrile, butyronitrile, and silicone solvents (e.g., silicone oils, polysiloxanes, cyclosilicones).

The term alcohol refers to a hydrocarbon derivative in which one or more hydrogen atoms have been replaced by an —OH group, known as hydroxyl group. Suitable alcohols for the present invention include linear, cyclic or branched $C_1$-$C_6$ alkyl alcohols and any mixtures thereof. It also includes commercially available alcohols. Examples of alcohols are methanol, ethanol, isopropanol, 1-propanol, 1-butanol, 1-pentanol, 3-methyl-1-butanol, tert-butanol, 1-octanol, benzyl alcohol and phenol.

The term room temperature in the context of the present invention means that the temperature is between 10° C. and 40° C., preferably between 15° C. and 30° C., more preferably between 20° C. and 25° C.

The term conventional purification techniques as used herein refers to the process wherein a product can be obtained in high purity, which can be carried out on an industrial scale such as solvent extraction, filtration, distillation, slurring, washing, phase separation, evaporation, centrifugation, isolation or crystallization.

As used herein, the term, solvent extraction refers to the process of separating components of a mixture by using a solvent which possesses greater affinity for one component, and may therefore separate said one component from at least a second component which is less miscible than said one component with said solvent.

The term filtration refers to the act of removing solid particles greater than a predetermined size from a feed comprising a mixture of solid particles and liquid. The expression filtrate refers to the mixture less the solid particles removed by the filtration process. It will be appreciated that this mixture may contain solid particles smaller than the predetermined particle size. The expression "filter cake" refers to residual solid material remaining on a feed side of a filtration element.

As used herein, the term slurring refers to any process which employs a solvent to wash or disperse a crude product.

As used herein, the term washing refers to the process of purifying a solid mass (e.g., crystals) by passing a liquid over and/or through the solid mass in order to remove soluble matter. The process includes passing a solvent, such as distilled water, over and/or through a precipitate obtained from filtering, decanting, or a combination thereof. For example, in one embodiment of the invention, washing includes contacting solids with solvent or solvent mixture, vigorously stirring (e.g., for two hours), and filtering. The solvent can be water, can be an aqueous solvent system, or can be an organic solvent system. Additionally, the washing can be carried out with the solvent having any suitable temperature. For example, the washing can be carried out with the solvent having a temperature between about 0° C. and about 100° C.

The term phase separation refers to a solution or mixture having at least two physically distinct regions.

The term crystallization refers to any method known to a person skilled in the art such as crystallization from single solvent or combination of solvents by dissolving the compound optionally at elevated temperature and precipitating the compound by cooling the solution or removing solvent from the solution or both. It further includes methods such as solvent/antisolvent or precipitation.

The term polymorphic form or polymorph refers to crystalline forms of the same pure compound in which the molecules have different arrangements and/or different conformation of the molecules. As a result, the polymorphic solids have different unit cells and hence display different physical properties, including those to packing, and various thermodynamic, spectroscopic, interfacial, and mechanical properties.

The term solvate refers to solid molecular compounds that have incorporated the crystallizing solvent molecule in their lattice. When the solvent incorporated in the solvate is water, the solvate is called hydrate. All solvates are formed with stoichiometric or non-nonstoichiometric proportions between the compound and the solvent of crystallization. Solvates can exhibit polymorphism, i.e they may exist in more than one polymorphic form.

The term solid form includes all solid materials, polymorphs, solvates (including hydrates), amorphous solids, salts and co-crystals.

The term purification and/or purifying as used herein refer to the process wherein a purified drug substance can be obtained, measured by HPLC preferably having a purity greater than 80%, more preferably greater than 85%, more preferably greater than 90%, more preferably greater than 95%, more preferably greater than 99%, more preferably greater than 99.5%, even more preferably greater than 99.9%. The term "industrial purification" refers to purifications, which can be carried out on an industrial scale such as solvent extraction, filtration, slurring, washing, phase separation, evaporation, centrifugation or crystallization.

The term olodaterol or pharmaceutically acceptable salt thereof, preferably olodaterol hydrochloride, in high chemical purity refers to a purity obtained by HPLC of at least 99%, preferably of at least 99.5%, most preferably of at least 99.9%, even more preferably of at least 99.95%, even most preferably of 100%.

The term olodaterol or pharmaceutically acceptable salt thereof, preferably olodaterol hydrochloride, in high enantiomeric purity refers to an enantiomeric purity of the R-enantiomer measured by chiral HPLC of at least 99.85%, more preferably of at least 99.90%, even more preferably of at least 99.95%, even more preferably of 100.00%.

The term pharmaceutically acceptable salt when characterizing olodaterol salts refers to a salt prepared from a base or their respective conjugated acids, which is acceptable for administration to a patient, such as a mammal. Such salts can be derived from pharmaceutically acceptable inorganic or organic acids, which include, but are not limited to hydrochloric, hydrobromic, sulfuric, phosphoric, nitric, methansulfonic, ethansulfonic, benzenesulfonic, p-toluenesulfonic, camphorsulfonic, 1,5-naphthalene disulfonic, formic, acetic, benzoic, malonic, malic, citric, fumaric, gluconic, glycolic, glutamic, lactic, maleic, L-tartaric, oxalic, mandelic, mucic, pantothenic, succinic, xinafoic (1-hydroxy-2-naphthoic acid) and cinnamic acid. Preferably, the pharmaceutically acceptable acid is hydrochloric acid.

The term (R)-camphorsulfonic acid refers either to (R)-(−)-camphorsulfonic acid or (1R)-(−)-10-camphorsulfonic acid. The term (S)-camphorsulfonic acid refers either to (S)-(+)-camphorsulfonic acid or (1S)-(+)-10-camphorsulfonic acid.

DETAILED DESCRIPTION OF THE INVENTION

Camphorsulfonate Salt of Intermediate (4)

The inventors have realized that the epoxide opening reaction of compound of formula (2) with amine (3) disclosed in prior art documents WO2005/111005 A1, WO 2007/020227 A1 and WO 2008/090193 A2 leads to desired advanced intermediate (4) in the form of free base or hydrochloride salt (previously shown in schemes 1, 2 and 4), but always with the presence of a significant amount of impurities, which are difficult to eliminate from final olodaterol. These impurities are compounds of formula IMP-1, IMP-2, IMP-3 and IMP-4 depicted below.

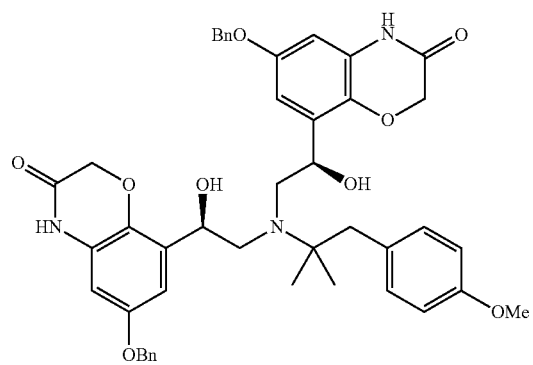
(IMP-1)

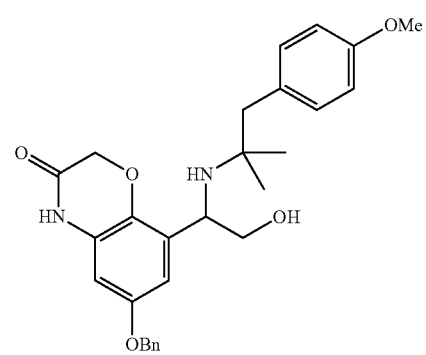
(IMP-2)

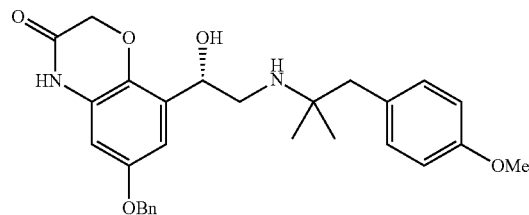
(IMP-3)

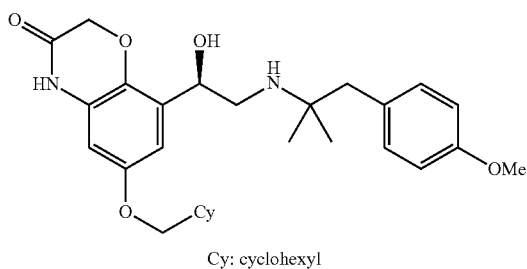

(IMP-4)

Cy: cyclohexyl

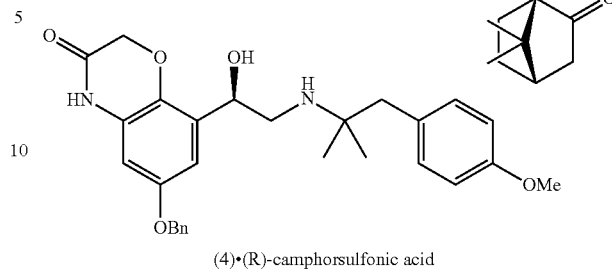

(4)·(R)-camphorsulfonic acid

The most significant being the dimer impurity (IMP-1), which is the consequence of a second addition of the product initially obtained with another epoxide (2), as well as the formation of another isomer (IMP-2) which is the result of the addition of the amine (3) to the secondary carbon of the epoxide (2). The inventors have unexpectedly found that purifying intermediate (4), obtained from the epoxide opening reaction, by formation of the camphorsulfonate salt significantly decreases the content of these impurities in a reproducible manner, and thus providing final olodaterol or salt thereof, preferably the R-enantiomer of olodaterol hydrochloride, in high chemical and enantiomeric purity and in high yield.

Thus, a first aspect of the present invention provides the camphorsulfonate salt of intermediate (4), compound of formula (4)-camphorsulfonic acid, and solid forms thereof, wherein PG is a hydroxyl protecting group as previously defined, preferably an aralkyl group, more preferably $C_1$-$C_{10}$alkyl substituted by a $C_6$-$C_{10}$aryl group, more preferably benzyl or p-methoxybenzyl, still more preferably benzyl. The camphorsulfonate salt of intermediate (4) is obtained in high chemical and enantiomeric purity and high yield, and has good stability.

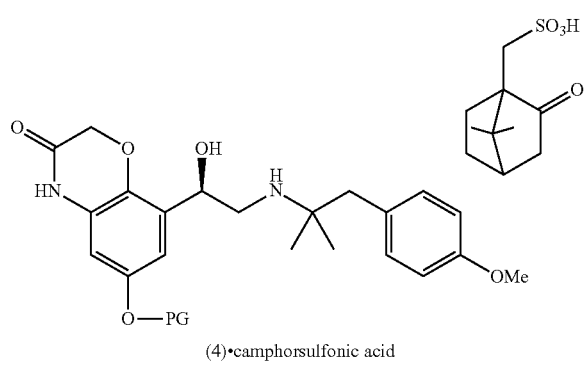

(4)·camphorsulfonic acid

The camphorsulfonic acid forming the salt of the invention may be the (R)-camphorsulfonic acid, the (S)-camphorsulfonic acid or mixtures thereof. In a preferred embodiment, the salt is the (R)-camphorsulfonate salt of intermediate (4). In another embodiment, the salt is the (S)-camphorsulfonate salt of intermediate (4). In a more preferred embodiment, the salt is the (R)-camphorsulfonate salt of intermediate (4), wherein PG is benzyl, whose structure is shown below.

In one embodiment, the molar ratio of intermediate (4) to the camphorsulfonic acid is 1:1.

In a particular embodiment, the camphorsulfonate salt of intermediate (4) is in solid form. Preferably, the camphorsulfonate salt of intermediate (4) is in crystalline solid form. In an alternative embodiment the camphorsulfonate salt of intermediate (4) is in non-crystalline (i.e. amorphous) solid form. More preferably, the camphorsulfonate salt of intermediate (4) is the (R)-camphorsulfonate salt, wherein PG is benzyl, in crystalline solid form. More preferably, the (R)-camphorsulfonate salt of intermediate (4), wherein PG is benzyl, is an anhydrous solid form. In still another embodiment, the (R)-camphorsulfonate salt of intermediate (4), wherein PG is benzyl, encompasses solvates (including hydrates). In one embodiment, a crystalline solid form of the camphorsulfonate salt of intermediate (4), wherein PG is benzyl, is characterized by at least one of the following:

a) a DSC thermogram showing an endothermic peak with an onset at 163-166° C., or b) an IR spectra showing the following bands at 2955, 1745, 1702, 1617, 1513, 1470, 1369, 1329, 1250, 1162, 1051, 1038, 852, 746, 700 $cm^{-1}$.

In a further embodiment, the (R)-camphorsulfonate salt of intermediate (4), wherein PG is benzyl, is characterized by a DSC thermogram showing an endothermic peak with an onset at 163-166° C.

Another embodiment, the (R)-camphorsulfonate salt of intermediate (4), wherein PG is benzyl, is characterized by an IR spectra showing the following bands at 2955, 1745, 1702, 1617, 1513, 1470, 1369, 1329, 1250, 1162, 1051, 1038, 852, 746, 700 $cm^{-1}$.

Figure 4:
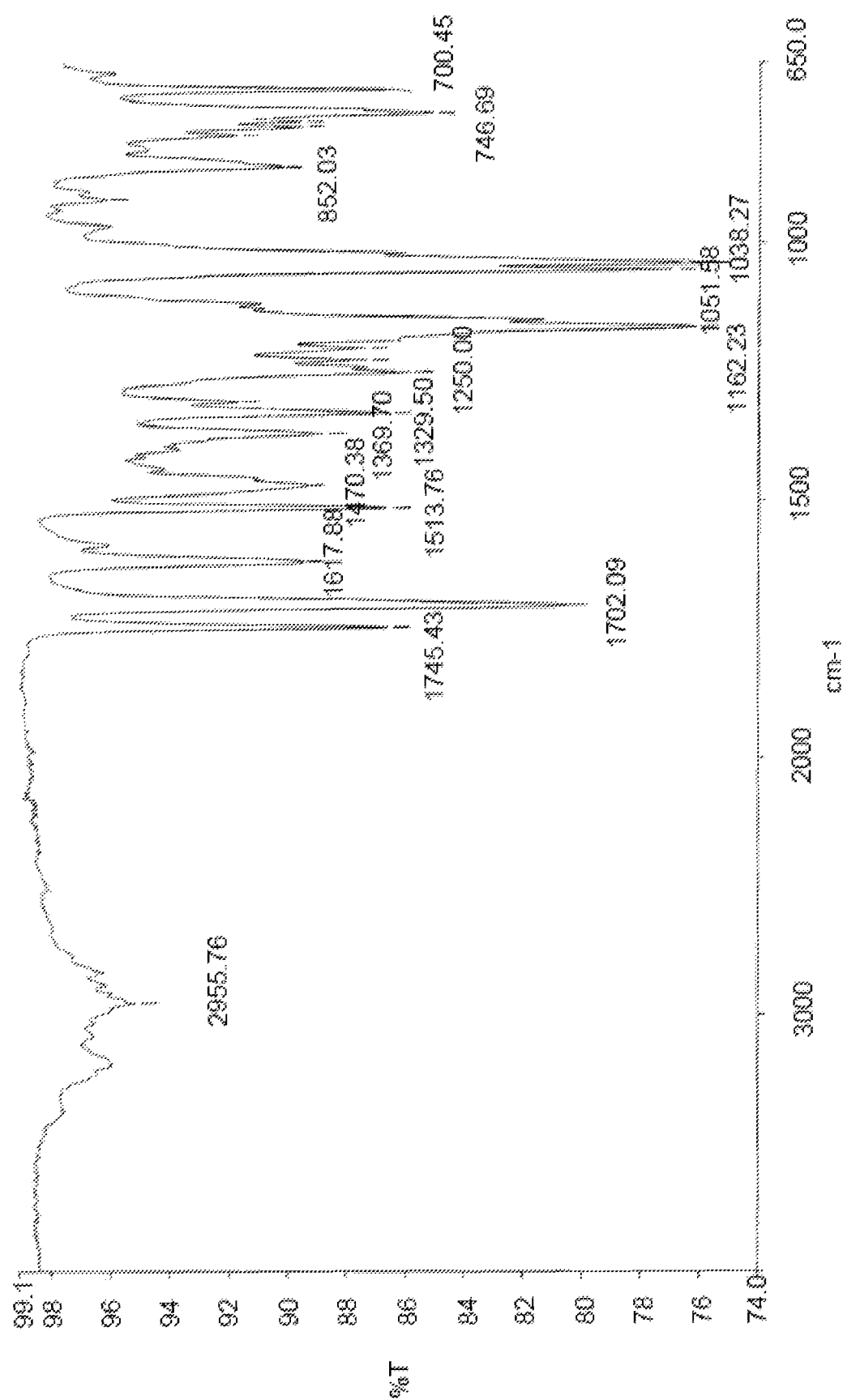
FIG. 4 shows the IR analysis of (R)-(−)-camphorsulfonate salt of intermediate (4), wherein PG is benzyl, prepared as in example 6.

In a further embodiment, the (R)-camphorsulfonate salt of intermediate (4), wherein PG is benzyl, is characterized in that it provides an IR spectrum substantially in accordance with FIG. 4.

In an alternative embodiment, the salt is the (S)-camphorsulfonate of intermediate (4), wherein PG is benzyl.

A second aspect of the present invention provides a process for preparing the camphorsulfonate salt of intermediate (4) as defined in the first aspect, comprising the steps of:

a) treating intermediate of formula (4), wherein PG is a hydroxyl protecting group as previously defined, with camphorsulfonic acid in the presence of a solvent or a mixture of solvents

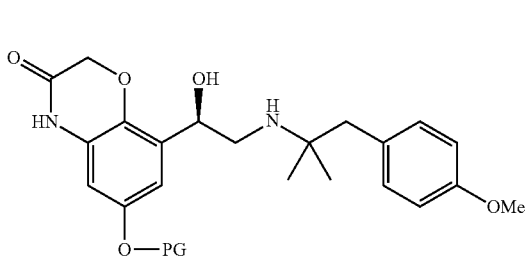

(4)

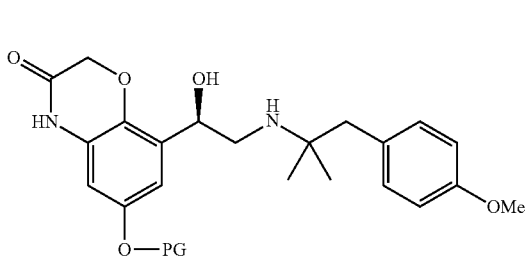

(4)·HX preferably PG is an aralkyl group, more preferably $C_1$-$C_{10}$alkyl substituted by a $C_6$-$C_{10}$aryl group, more preferably benzyl or p-methoxybenzyl, and b) isolating the camphorsulfonate salt obtained in step a).

The molar ratio of camphorsulfonic acid to intermediate (4) used in step a) of the above mentioned process is preferably at least 1:1, preferably from 1:1 to 2:1, still more preferably from 1:1 to 1.1:1.

Suitable solvents in step a) are organic solvents as previously defined. Preferably, the solvent comprises an organic solvent, water or mixtures thereof. Suitable organic solvent is a polar solvent. Preferably, the solvent comprises a mixture of two polar solvents. Suitable polar solvents are ether and ester solvents. Suitable ethers are diethyl ether, dipropyl ether, diphenyl ether, isopropyl ether, tert-butyl methyl ether, tetrahydrofuran and 1,4-dioxane and mixtures thereof. Suitable esters are ethyl formate, methyl acetate, ethyl acetate, ethyl malonate and mixtures thereof. More preferably, the polar solvent comprises a mixture of an ether and ester. More preferably, the organic solvent is a mixture of ester (in particular ethyl acetate) and tetrahydrofuran, preferably, in a ratio from 15:1 to 1:15 (v/v). More preferably, the solvent comprises a mixture of an ester (in particular ethyl acetate) and tetrahydrofuran in a ratio from 15:1 to 1:1 (v/v). Also more preferably, an ester (in particular ethyl acetate) and tetrahydrofuran in a ratio from 15:1 to 10:1 (v/v) as the yield is increased.

Step b), isolation of the salt obtained in step a), may be carried out by conventional means, such as by filtration optionally followed by washing. Preferably the washing is carried out with a mixture of ester (in particular ethyl acetate) and tetrahydrofuran, preferably in a ratio from 6:1 to 4:1 (v/v).

In a particular embodiment, the camphorsulfonate salt may be purified by means of conventional purification techniques. In a preferred embodiment, the camphorsulfonate salt may be purified by crystallization. In still more preferred embodiment, the (R)-camphorsulfonate salt of intermediate (4), preferably wherein PG is benzyl, is purified by crystallization. In another preferred embodiment, the (S)-camphorsulfonate salt of intermediate (4), preferably wherein PG is benzyl, is purified by crystallization. A third aspect of the present invention provides a process for the manufacture of olodaterol or a pharmaceutical salt thereof, preferably the R-enantiomer of olodaterol hydrochloride, comprising the steps of:

a) providing camphorsulfonate salt of compound (4) according to the first aspect of the invention b) optionally treating the camphorsulfonate salt of compound (4) with hydrochloric acid, to provide compound of formula (4).HX, wherein HX is hydrochloric acid c) removing the hydroxyl protecting group PG from the products of steps a) or b), by hydrogenation in the presence of a catalyst and an organic solvent to provide olodaterol or a pharmaceutical salt thereof, preferably the R-enantiomer of olodaterol hydrochloride, and optionally, treating olodaterol obtained in step d) with a pharmaceutically acceptable acid to provide a pharmaceutically acceptable salt thereof, preferably the R-enantiomer of olodaterol hydrochloride The present invention also encompasses a process for the purification of olodaterol or salt thereof, preferably the R-enantiomer of olodaterol hydrochloride, said process comprising preparing the camphorsulfonate salt of intermediate (4) according to the first aspect of the invention, preferably the (R)-camphorsulfonate salt, according to the process of the second aspect and converting it to olodaterol or salt thereof, preferably the R-enantiomer of olodaterol hydrochloride.

1,1-Dimethyl-2-(4-methoxyphenyl)ethyl Amine L-tartrate Salt

The inventors of the present invention have realized that prior art 1,1-dimethyl-2-(4-methoxyphenyl)ethyl amine hydrochloride salt rapidly absorbs water up to 4% by weight, after remaining under ambient conditions, and rapidly transforms into a hemihydrate. This behavior not only implies handling problems but also the water absorbed may react with the amine intermediate to generate further impurities. In addition, the 1,1-dimethyl-2-(4-methoxyphenyl)ethyl amine hydrochloride salt provided by reproducing prior art contains at least two significant impurities, being compounds of formula A and formula B, see Scheme 6. These impurities react as nucleophiles in a similar way as 1,1-dimethyl-2-(4-methoxyphenyl)ethyl amine (3) does in their epoxide-opening reaction with (R)-6-benzyloxy-8-oxiranyl-4H-benzo[1,4]oxazin-3-one (2), to provide impurity compounds (8) and (9), which are difficult to separate from olodaterol intermediate (4) and from olodaterol final product, resulting in a noticeable decrease of yield of olodaterol.

Scheme 6

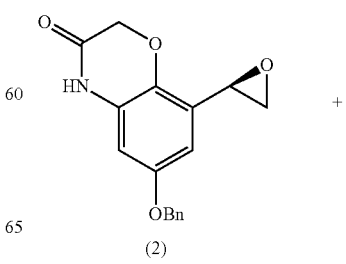

(2)

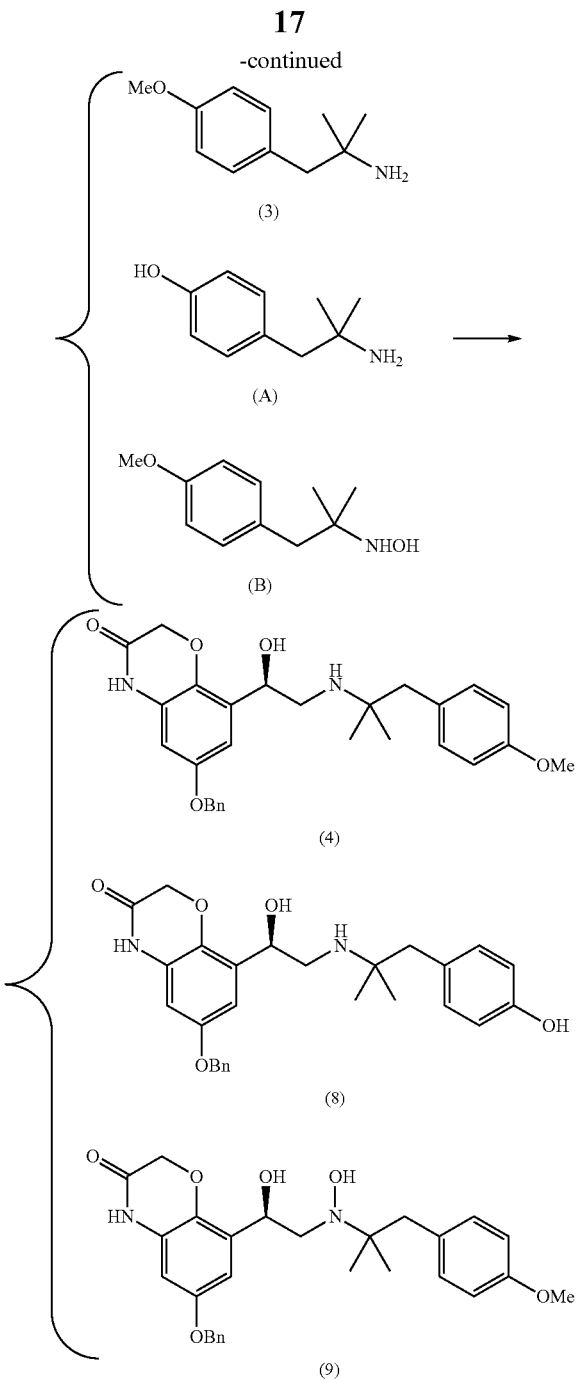

(3)

(A)

(B)

(4)

(8)

(9)

The purification of 1,1-dimethyl-2-(4-methoxyphenyl) ethyl amine hydrochloride salt, the compound (3).HCl, by conventional purification techniques in various solvents was unsuccessful. See test example 1 in the experimental section. On the other hand, the present inventors have surprisingly found that 1,1-dimethyl-2-(4-methoxyphenyl)ethyl amine L-tartrate salt is prepared in high purity, with low content of impurities A and B, and in high yield in a reproducible manner. In addition, the 1,1-dimethyl-2-(4-methoxyphenyl) ethyl amine L-tartrate salt is not hygroscopic and stable over time which makes this intermediate ease to handle at industrial scale production.

Thus, a fourth aspect of the present invention provides 1,1-dimethyl-2-(4-methoxyphenyl)ethyl amine L-tartrate salt, compound of formula (3).L-tartaric acid, wherein the molar ratio of 1,1-dimethyl-2-(4-methoxyphenyl)ethyl amine to L-tartaric acid is 1:1. Alternatively, the molar ratio of 1,1-dimethyl-2-(4-methoxyphenyl)ethyl amine to L-tartaric acid is 2:1.

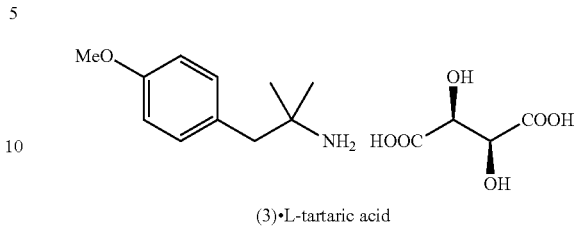

(3)·L-tartaric acid

The 1,1-dimethyl-2-(4-methoxyphenyl)ethyl amine L-tartrate salt according to the fourth aspect is obtained in high chemical purity and high yield, and has good stability.

Advantageously, the 1,1-dimethyl-2-(4-methoxyphenyl) ethyl amine L-tartrate salt of the present invention is useful for preparing olodaterol or pharmaceutically acceptable salt thereof, preferably olodaterol hydrochloride, in high purity and high yield in a reproducible manner, having low concentrations of undesired impurities of formula (8) and (9).

In an embodiment of the fourth aspect the present invention relates to solid forms of 1,1-dimethyl-2-(4-methoxyphenyl)ethyl amine L-tartrate salt as defined in said fourth aspect.

In a further preferred embodiment of the fourth aspect, the 1,1-dimethyl-2-(4-methoxyphenyl)ethyl amine L-tartrate salt is in a crystalline solid form. In a more preferred embodiment, the crystalline solid form of the L-tartrate salt is in anhydrous form.

In still a further embodiment of the fourth aspect the 1,1-dimethyl-2-(4-methoxyphenyl)ethyl amine L-tartrate salt is in a non-crystalline (amorphous) solid form.

In still a further embodiment the 1,1-dimethyl-2-(4-methoxyphenyl)ethyl amine L-tartrate salt is in the form of a solvate (including hydrates).

In a further embodiment, the 1,1-dimethyl-2-(4-methoxyphenyl)ethyl amine L-tartrate salt is characterized by a DSC thermogram showing an endothermic peak with an onset at 209-211° C.

In a further embodiment, the 1,1-dimethyl-2-(4-methoxyphenyl)ethyl amine L-tartrate salt is characterized in that it provides a DSC thermogram substantially in accordance with FIG. 1.

Figure 2:
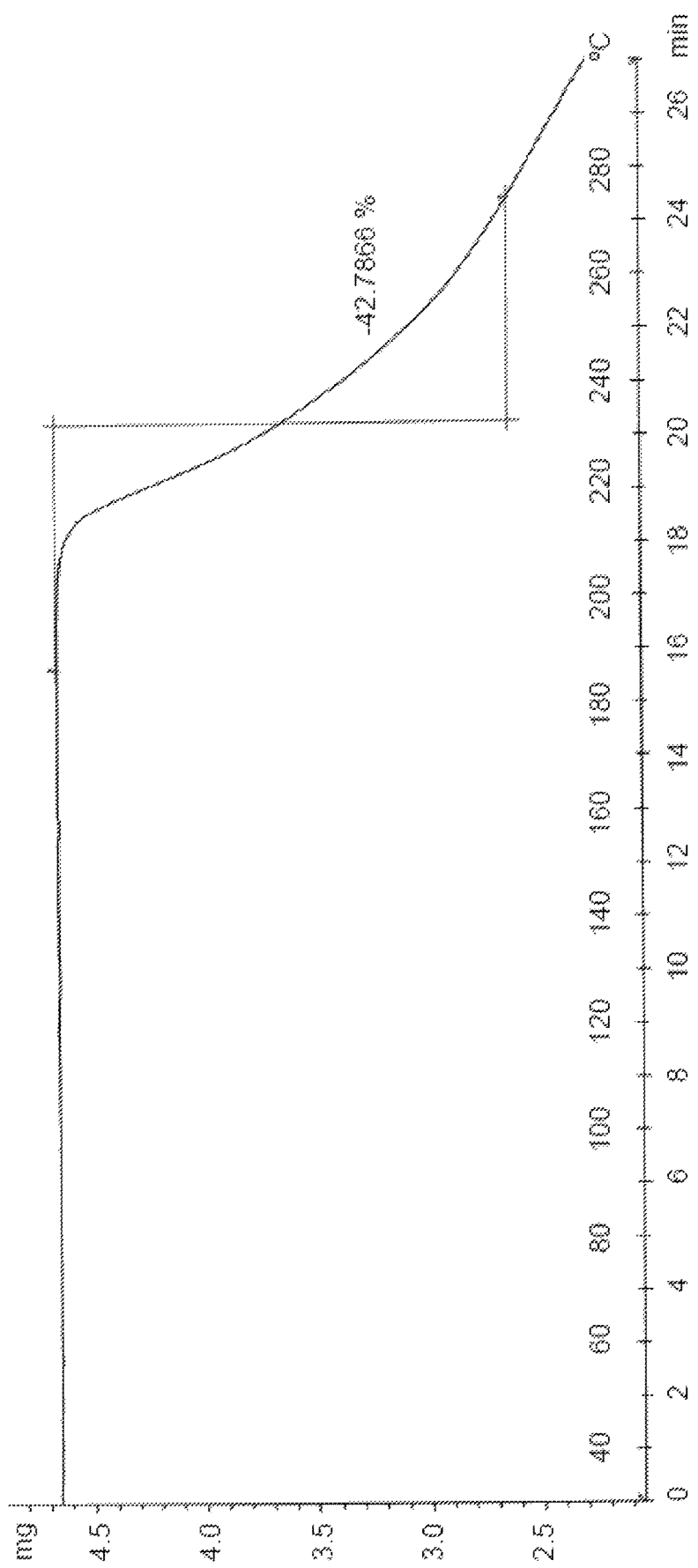
FIG. 2 shows the TG analysis of 1,1-dimethyl-2-(4-methoxyphenyl)ethyl amine L-tartrate salt prepared as in example 2.

In a further embodiment, the 1,1-dimethyl-2-(4-methoxyphenyl)ethyl amine L-tartrate salt is characterized in that it provides a TG thermogram substantially in accordance with FIG. 2.

Another embodiment of the fourth aspect, the 1,1-dimethyl-2-(4-methoxyphenyl)ethyl amine L-tartrate salt is characterized by an IR spectra showing the following bands at 3386, 3283, 3207, 2995, 2956, 2908, 1648, 1507, 1252, 1121 and 823 cm$^{-1}$.

Figure 3:
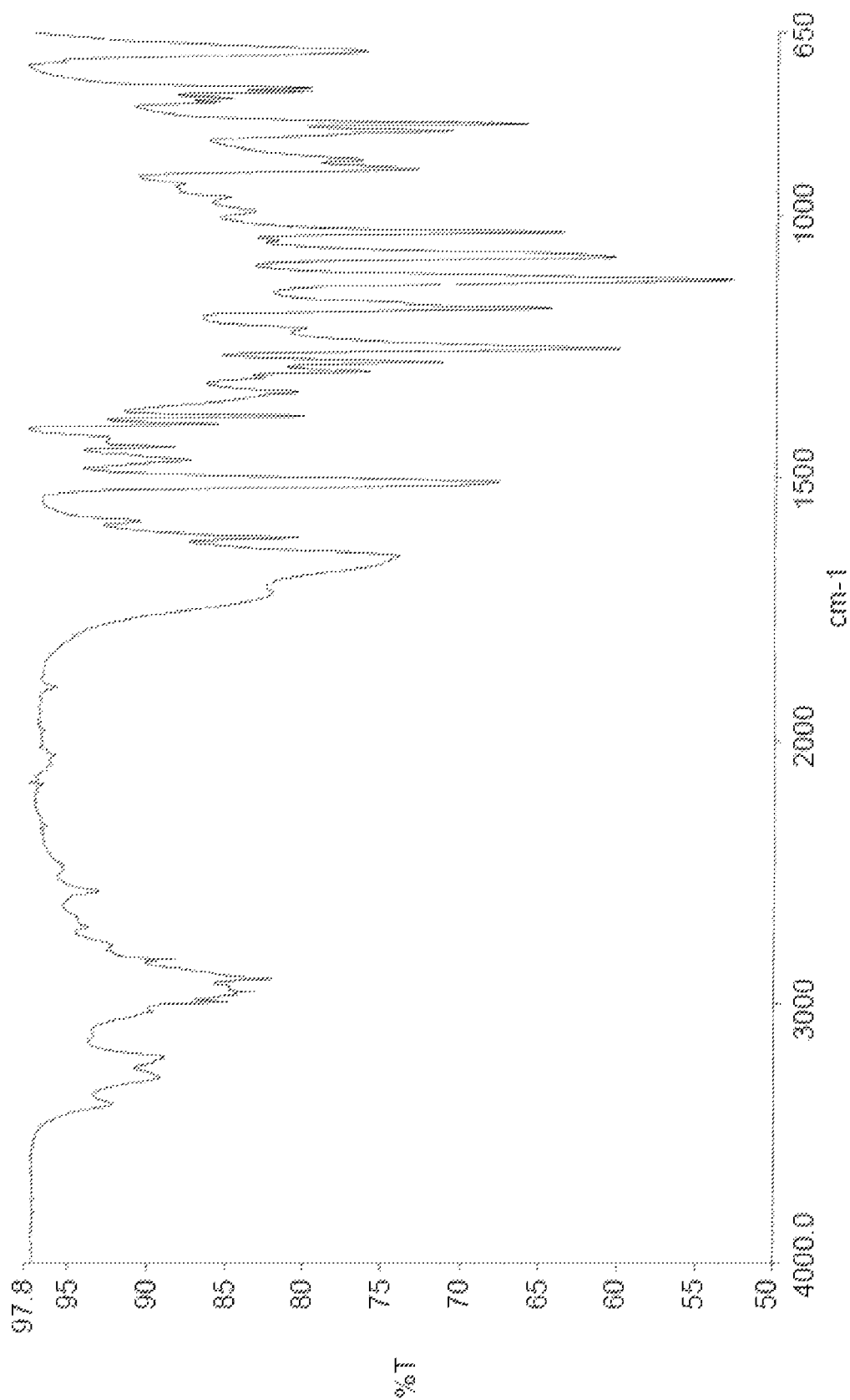
FIG. 3 shows the IR analysis of 1,1-dimethyl-2-(4-methoxyphenyl)ethyl amine L-tartrate salt prepared as in example 2.

In a further embodiment, the 1,1-dimethyl-2-(4-methoxyphenyl)ethyl amine L-tartrate salt is characterized in that it provides an IR spectrum substantially in accordance with FIG. 3.

In a further embodiment, the invention encompasses 1,1-dimethyl-2-(4-methoxyphenyl)ethyl amine L-tartrate salt in pure form or when admixed with other materials, for example, other polymorphs, solvates or remaining reaction solvents or side products or byproducts.

A fifth aspect of the present invention provides a process for preparing 1,1-dimethyl-2-(4-methoxyphenyl)ethyl amine L-tartrate salt as defined in the fourth aspect, which comprises the steps of:

a) treating 1,1-dimethyl-2-(4-methoxyphenyl)ethyl amine, compound of formula (3), with L-tartaric acid in the presence of a solvent, preferably in the presence of a mixture of an organic solvent and water

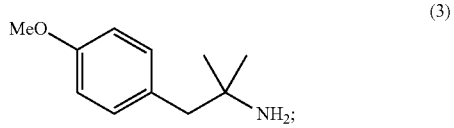

(3)

and b) isolating the L-tartrate salt obtained in step a).

The molar ratio of 1,1-dimethyl-2-(4-methoxyphenyl) ethyl amine to L-tartaric acid used in the above mentioned process is at least 1:1. Alternatively, the molar ratio of 1,1-dimethyl-2-(4-methoxyphenyl)ethyl amine to L-tartaric acid used in the above mentioned process is 2:1.

Suitable solvents in step a) are organic solvents as defined above. Preferably, the solvent comprises an organic solvent, water or mixtures thereof. Suitable organic solvent is a polar solvent. Preferably, the solvent comprises a mixture of a polar solvent and water. Suitable polar solvents are alcohols, ester and ketone solvents. More preferably, the solvent comprises a mixture of an alcohol and water. Suitable alcohols are linear or branched C1-C6 alcohols, such as methanol, ethanol, 1-propanol, isopropanol and mixtures thereof. Preferably, the solvent comprises a mixture of an alcohol and water in a ratio from 10:1 to 1:10 (v/v). More preferably, the solvent comprises a mixture of an alcohol and water in a ratio from 10:1 to 1:1 (v/v). Also more preferably, the solvent comprises a mixture of an alcohol and water in a ratio from 7:1 to 3:1 (v/v) as the yield is increased.

Step b), isolation of the salt obtained in step a), may be carried out by conventional means, such as by filtration optionally followed by washing.

In another embodiment, the L-tartrate salt may be purified by means of conventional purification techniques. In a preferred embodiment, the L-tartratre salt may be purified by crystallization.

In an embodiment of the process according to the fifth aspect, the 1,1-dimethyl-2-(4-methoxyphenyl)ethyl amine of formula (3) is prepared comprising the steps of:

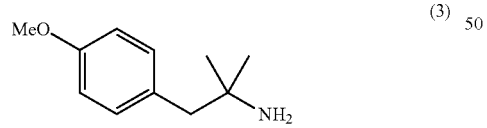

(3)

a) treating the compound of formula (6) with a methylating agent in the presence of a base and an organic solvent

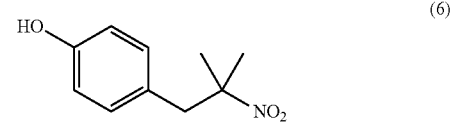

(6)

to provide the compound of formula (7)

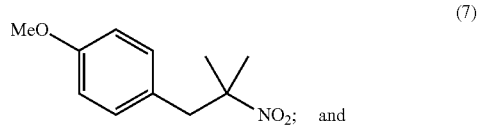

(7)

and b) converting the compound of formula (7) obtained in step a) in the amine of formula (3) by hydrogenation in the presence of a catalyst and an organic solvent.

Advantageously, the 1,1-dimethyl-2-(4-methoxyphenyl) ethyl amine L-tartrate salt according to the fourth of the present invention obtainable through the process according to the fifth aspect, contains less than 0.1% (w/w) of impurity of formula (A) and/or less than 0.1% (w/w) of impurity of formula (B), relative to the amount of the 1,1-dimethyl-2-(4-methoxyphenyl)ethyl amine L-tartrate salt as measured by HPLC. Preferably, the 1,1-dimethyl-2-(4-methoxyphenyl)ethyl amine L-tartrate salt of the present invention contains less than 0.05% (w/w) of impurity of formula (A) and/or less than 0.05% (w/w) of impurity of formula (B), relative to the amount of the 1,1-dimethyl-2-(4-methoxyphenyl)ethyl amine L-tartrate salt as measured by HPLC.

1,1-Dimethyl-2-(4-methoxyphenyl)ethyl Amine Maleate Salt

As explained with respect to the 1,1-dimethyl-2-(4-methoxyphenyl)ethyl amine L-tartrate salt, the use of the hydrochloride salt in the synthesis of olodaterol entails several difficulties due to its hygroscopicity including the poor effect of purification of impurities, such as compounds of formula (A) and (B) depicted in Scheme 6 and also another impurity (C) whose chemical nature has not been established. The inventors have surprisingly found that the use of the 1,1-dimethyl-2-(4-methoxyphenyl)ethyl amine maleate salt allows reducing or even eliminating the above-mentioned impurity. Thus, the use of this salt is advantageous in the production of olodaterol or pharmaceutically acceptable salts thereof with very low content of impurities.

Thus, a sixth aspect of the present invention provides 1,1-dimethyl-2-(4-methoxyphenyl)ethyl amine maleate salt, compound of formula (3)-maleic acid and solid forms thereof.

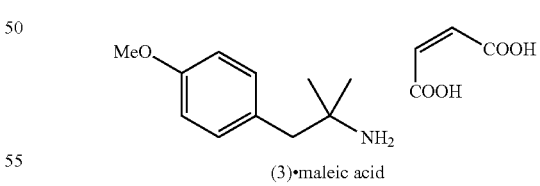

(3)·maleic acid

The 1,1-dimethyl-2-(4-methoxyphenyl)ethyl amine maleate salt according to the sixth aspect is obtained in high chemical purity and high yield, and has good stability.

In one embodiment, the molar ratio of 1,1-dimethyl-2-(4-methoxyphenyl)ethyl amine to maleic acid is 2:1. Alternatively, the molar ratio of 1,1-dimethyl-2-(4-methoxyphenyl) ethyl amine to maleic acid is 1:1.

In a particular embodiment, the 1,1-dimethyl-2-(4-methoxyphenyl)ethyl amine maleate salt is in solid form. Preferably, the 1,1-dimethyl-2-(4-methoxyphenyl)ethyl amine maleate salt is in a crystalline solid form. In an alternative embodiment the 1,1-dimethyl-2-(4-methoxyphenyl)ethyl amine maleate salt is in a non-crystalline (i.e. amorphous) solid form.

A seventh aspect of the present invention relates to a process for preparing the maleate salt as defined in the sixth aspect, which comprises the steps of:

a) treating amine of formula (3) with maleic acid in the presence of a solvent

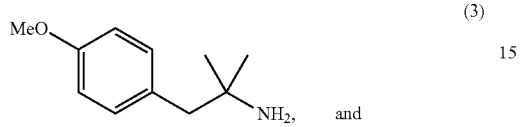
(3)

and b) isolating the maleate salt obtained in step a).

The molar ratio of 1,1-dimethyl-2-(4-methoxyphenyl)ethyl amine to maleic acid used in step a) of the above mentioned process is preferably at least 1:1, more preferably from 1:1 to 2:1, still more preferably from 1:1 to 1.5:1, even more preferably from 1:1 to 1.1:1.

Suitable solvents in step a) are organic solvents as previously defined. Preferably, the solvent comprises an organic solvent, water or mixtures thereof. Suitable organic solvent is a polar solvent. Preferably, the solvent comprises an organic solvent, water or mixtures thereof. Suitable polar solvents are alcohols, esters, ethers and solvents. Preferably, polar solvents are esters and ethers. Suitable esters may be ethyl formate, methyl acetate, ethyl acetate, isopropyl acetate, butyl acetate, isobutyl acetate and ethyl malonate and mixtures thereof. Suitable ethers may be diethyl ether, dipropyl ether, diphenyl ether, isopropyl ether, tert-butyl methyl ether, tetrahydrofuran and 1,4-dioxane and mixtures thereof. More preferably, the solvent used in step a) is an ester solvent such as methyl acetate, ethyl acetate, isopropyl acetate and mixtures thereof as the yield is increased.

Step b), isolation of the salt obtained in step a), may be carried out by conventional means, such as by filtration optionally followed by washing.

In a particular embodiment, the maleate salt may be purified by means of conventional purification techniques. In a preferred embodiment, the maleate salt may be purified by crystallization.

In an embodiment of the process according to the fifth aspect, the 1,1-dimethyl-2-(4-methoxyphenyl)ethyl amine of formula (3) is prepared comprising the steps of:

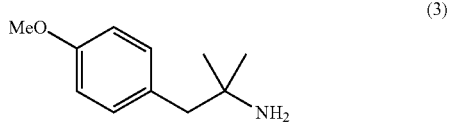
(3)

a) treating the compound of formula (6) with a methylating agent in the presence of a base and an organic solvent

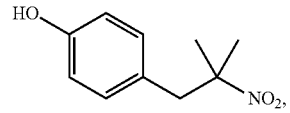
(6)

to provide the compound of formula (7)

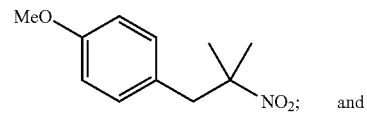
(7)

and b) converting the compound of formula (7) obtained in step a) in the amine of formula (3) by hydrogenation in the presence of a catalyst and an organic solvent.

Process for the Manufacture of a Pharmaceutically Acceptable Salt of Olodaterol Comprising the 1,1-dimethyl-2-(4-methoxyphenyl)ethyl Amine L-tartrate Salt, the 1,1-dimethyl-2-(4-methoxyphenyl)ethyl Amine Maleate Salt and/or the Camphorsulfonate Salt of Intermediate (4)

A further embodiment of the third aspect of the present invention provides a process for preparing olodaterol or a pharmaceutically acceptable salt thereof, preferably the R-enantiomer of olodaterol hydrochloride, comprising at least the steps of:

a1) treating the L-tartrate salt, compound of formula (3).L-tartaric acid, or as defined in the fourth aspect, which may be obtained through the process according to the fifth aspect,

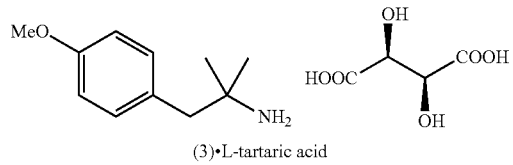
(3)·L-tartaric acid with a base in the presence of a mixture of an organic solvent and water to provide the amine of formula (3)

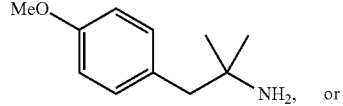
(3)

or a2) treating the maleate salt, compound of formula (3)-maleic acid, as defined in the sixth aspect, which may be obtained through the process according to the seventh aspect,

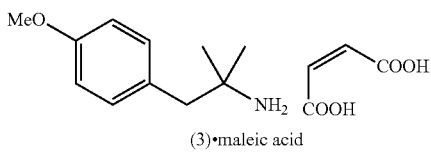

(3)·maleic acid

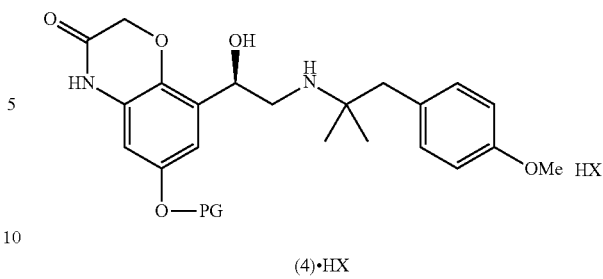

(4)·HX with a base in the presence of a mixture of an organic solvent and water to provide the amine of formula (3)

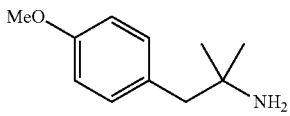

(3)

b) reacting the amine of formula (3) obtained in step a1) or a2) with epoxide of formula (2), wherein PG is a hydroxyl protecting group, in the presence of an organic solvent

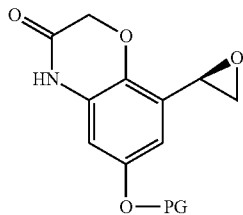

(2)

to provide the compound of formula (4)

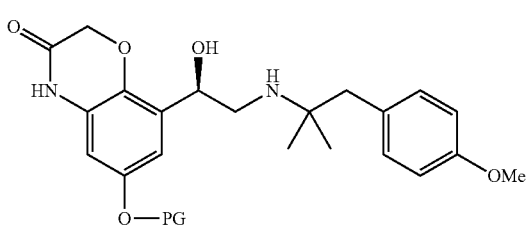

(4)

c) optionally, treating the compound of formula (4) obtained in step b) with a pharmaceutically acceptable acid HX, preferably wherein the acid HX is camphorsulfonic acid or hydrochloric acid, most preferably camphorsulfonic acid to provide compound of formula (4).HX, wherein PG is a hydroxyl protecting group as defined above d) removing the hydroxyl protecting group PG from the products obtained in step b) or c), when present by hydrogenation in the presence of a catalyst and an organic solvent to provide olodaterol or a pharmaceutical salt thereof, preferably olodaterol hydrochloride, and e) optionally, treating olodaterol obtained in step d) with a pharmaceutically acceptable acid to provide a pharmaceutically acceptable salt thereof.

In one embodiment, the process proceeds through step a1), preferably through step a1) and wherein HX in step c) is hydrochloric acid. In an alternative embodiment, the process proceeds through step a2), preferably through step a2) and wherein HX in step c) is hydrochloric acid.

Suitable bases for step a1) and for step a2) may be inorganic bases selected from hydroxides, carbonates and bicarbonates of calcium, sodium, magnesium, potassium, lithium and caesium and mixtures thereof. The amount of base used may be at least in a molar ratio of 1:1 of base to the L-tartrate salt, preferably in a molar ratio of from 1:1 to 10:1, more preferably 1:1 to 5:1, still more preferably from 1:1 to 2.5:1. The amount of base used may be at least in a molar ratio of 1:1 of base to the maleate salt, in particular in a molar ratio of at least 2:1, preferably in a molar ratio of from 1:1 to 10:1, more preferably 1:1 to 5:1, still more preferably from 1:1 to 2.5:1.

PG is a hydroxyl protecting group commonly known in the art for protecting phenol groups. As an example, their introduction and removal are discussed in T. W. Greene and G. M. Wuts, *Protecting groups in Organic Synthesis*, Third Edition, Wiley, New York, 1999. Suitable hydroxyl protecting groups are those which are stable under alkaline conditions. More preferably, the hydroxyl protecting group can be deprotected by hydrogenation such as aralkyl groups and heteroaralkyl groups and the like.

Alkyl means straight-chain or branched hydrocarbon chain radical containing no insaturation having from 1 to 10 carbon atoms, represented as $C_1$-$C_{10}$ alkyl. Such alkyl groups may be selected from methyl, ethyl, n-propyl, isopropyl, n-butyl, isobutyl, sec-butyl, tert-butyl, straight- or branched-pentyl, straight- or branched-hexyl, straight- or branched-heptyl, straight- or branched-nonyl or straight- or branched-decyl. Preferably the alkyl group is $C_1$-$C_4$ alkyl.

Aryl means an aromatic hydrocarbon radical having 6 to 10 carbon atoms such as phenyl or naphthyl. The aryl radical may be optionally substituted by one or more substituents such as OH, SH, halo, alkyl, phenyl, alkoxy, haloalkyl, nitro, cyano, acyl as defined herein.

Aralkyl means $C_1$-$C_{10}$ alkyl as defined above substituted with $C_6$-$C_{10}$ aryl as defined above. Preferably, the aralkyl group is a $C_1$-$C_4$alkyl group, substituted by a $C_6$-$C_{10}$ aryl group such as, phenyl, tolyl, xylyl and naphthyl. The $C_6$-$C_{10}$ aryl groups may also be substituted by one or more substituents on the ring. Suitable substituents are selected from alkyl, alkoxy, halogen, as defined herein and nitro. The preferred substituents are alkyl and alkoxy groups. Preferred aralkyl groups are 4-methylbenzyl, 2-methylbenzyl, 4-methoxybenzyl or p-methoxybenzyl, 2-methoxybenzyl, 2,4-dimetoxybenzyl, 3,4-dimetoxybenzyl, 2,6-dimetoxybenzyl, 4-nitrobenzyl, 2-nitrobenzyl or o-nitrobenzyl, 2,4-dinitrobenzyl, 4-chlorobenzyl and 2-chlorobenzyl. More preferably, the aralkyl is benzyl or p-methoxybenzyl. Still more preferably, the aralkyl is benzyl.

Heteroaralkyl means straight-chain or branched aralkyl as defined above, which may include one of the $C_6$-$C_{10}$ aryl-$C_1$-$C_{10}$ alkyl groups mentioned hereinbefore, substituted by one or more heterocyclic groups. Preferably, the aralkyl group is $C_6$-$C_{10}$ aryl-$C_1$-$C_4$ alkyl substituted by one or more heterocyclic groups.

In an embodiment, the hydroxyl protecting group PG are those which can be deprotected by hydrogenation such as 4-methylbenzyl, 2-methylbenzyl, 4-methoxybenzyl, 2-methoxybenzyl, 2,4-dimethoxybenzyl, 3,4-dimethoxybenzyl, 2,6-dimethoxybenzyl, 4-nitrobenzyl, 2-nitrobenzyl, 2,4-dinitrobenzyl, 4-chlorobenzyl and 2-chlorobenzyl. Preferably, the hydroxyl protecting group PG is benzyl and 4-methoxybenzyl. More preferably, the hydroxyl protecting group PG is benzyl.

Intermediate compound of formula (2) is known in the art. Preferably, compound of formula (2) wherein the hydroxyl protecting group is benzyl, (R)-6-benzyloxy-8-oxiranyl-4H-benzo[1,4]oxazin-3-one, is prepared according to prior art document WO 2008/090193 A2.

The organic solvent of step b) is as defined above. Preferably, the organic solvent is selected from the group consisting of an ether solvent (e.g., diethyl ether, dipropyl ether, diphenyl ether, isopropyl ether, tert-butyl methyl ether, tetrahydrofuran, 2-methyltetrahydrofuran, 1,4-dioxane, methyl phenyl ether or anisole), an aromatic hydrocarbon solvent (e.g., benzene, toluene, o-xylene, m-xylene, and p-xylene), alcohol solvents (e.g., methanol, ethanol, isopropanol, 1-propanol, 2-methyl-1-propanol, 1-butanol, 2-butanol, 1-pentanol, 3-methyl-1-butanol, tert-butanol, 1-octanol, benzyl alcohol, phenol, trifluoroethanol, glycerol, ethylene glycol, propylene glycol, m-cresol), ketone solvents (e.g., acetone, methyl ethyl ketone or 2-butanone, methyl isobutyl ketone, cyclohexanone, cyclopentanone, 3-pentanone), ester solvents (e.g., ethyl formate, methyl acetate, ethyl acetate, isopropyl acetate, butyl acetate, isobutyl acetate, ethyl malonate) and N,N-dimethylformamide, N,N,-dimethylacetamide, dimethylsulfoxide and acetonitrile, propionitrile and butyronitrile. More preferably, the organic solvent of step b) is selected from 2-methyltetrahydrofuran, 1,4-dioxane, anisole, toluene, ethylene glycol and acetonitrile.

In another embodiment, step b) may be conducted without the presence of an organic solvent.

Suitable pharmaceutically acceptable acid HX of step c) is selected from hydrochloric, hydrobromic, sulfuric, methansulfonic, ethansulfonic, p-toluensulfonic, camphorsulfonic, formic, acetic, malic, succinic, fumaric, glycolic, citric, fumaric, benzoic, malonic, maleic, L-tartaric, D-tartaric, ditoluyl-L-tartaric, ditoluyl-D-tartaric, dibenzoyl-L-tartaric, dibenzoyl-D-tartaric, oxalic, mandelic and 1-hydroxy-2-naphthoic acid. Preferably, the pharmaceutically acceptable acid of step c) is hydrochloric acid, camphorsulfonic, fumaric, benzoic, maleic, L-tartaric, D-tartaric, ditoluyl-L-tartaric and ditoluyl-D-tartaric, oxalic and mandelic acid. More preferably, the pharmaceutically acceptable acid HX of step c) is hydrochloric acid or camphorsulfonic acid, still more preferably hydrochloric acid, even more preferably camphorsulfonic acid.

In a preferred embodiment, the pharmaceutically acceptable salt of olodaterol is the hydrochloride salt, prepared by the process of the invention, which may be further purified. More preferably, the pharmaceutically acceptable salt of olodaterol, preferably olodaterol hydrochloride, may be purified by recrystallization.

In another preferred embodiment, step c) is carried out and the HX acid is camphorsulfonic acid, providing the camphorsulfonate salt of intermediate (4) as defined in the first aspect. Preferably, step c) further comprises converting the camphorsulfonate salt of intermediate (4) (i.e. HX is camphorsulfonic acid) into the hydrochloride salt of intermediate (4) (i.e. HX is hydrochloric acid). This involves treating the camphorsulfonate salt of compound (4), wherein PG is a hydroxyl protecting group as defined above, with hydrochloric acid (which may be present either as gas or as an aqueous solution or generated in situ, for example from an alkylsilyl halogenide in the presence of a protic solvent (such as an alcohol; i.e. methanol, ethanol, isopropanol, 1-propanol and 1-butanol) in the presence of a suitable organic solvent or mixtures of solvents. Suitable organic solvents may be selected from alcohols, ethers, esters, chlorinated hydrocarbons and mixtures thereof or aqueous mixtures thereof. Preferably, the organic solvent is selected from the group consisting of alcohols, ethers and esters.

In a more preferred embodiment, the camphorsulfonate salt of intermediate (4) is converted into the free base (i.e. compound of formula (4)), for example by treatment with a suitable base (which may be inorganic bases selected from hydroxides, carbonates and bicarbonates of calcium, sodium, magnesium, potassium, lithium and caesium and mixtures thereof), preferably in the presence of a suitable organic solvent as previously defined, preferably a polar solvent such as an ester, and ether or mixtures thereof. Compound of formula (4) free base is then reacted with hydrochloric acid (which may be present either as gas or as an aqueous solution or generated in situ, for example from an alkylsilyl halogenide in the presence of a protic solvent (such as an alcohol; i.e. methanol, ethanol, isopropanol, 1-propanol and 1-butanol) in the presence of an organic solvent as previously defined, to provide the corresponding salt of intermediate (4). More preferably, the salt of intermediate (4) is isolated, for example by filtration optionally followed by washing (such as washing with an ester, preferably ethyl acetate).

The hydrogenation step d) is conducted in the presence of a catalyst and an organic solvent. Suitable catalysts are selected from Pd, Pt, Rh, Ru, Ni, Fe, Zn and Ir catalyst. Preferably, suitable catalyst are selected form palladium (0) (Pd(0)), palladium hydroxide (Pd(OH)$_2$), palladium on activated carbon (Pd/C), palladium on alumina, palladium on carbon powder, platinum, platinum on activated carbon and Raney™ nickel. A combination of catalysts may also be used. Most preferably, the catalyst is palladium on activated carbon and palladium hydroxide (Pd(OH)$_2$). The amount of catalyst is not critical and may be equal or less than 10% by weight to the amount of compound of formula (4). Moreover, the hydrogenation takes place at a hydrogen pressure range of from 0.5 to 10 atm. Most preferably, the hydrogen pressure is from 0.5 to 5 atm since fewer impurities are generated.

In a particular embodiment of the third aspect of the present invention, the process for preparing the R-enantiomer of olodaterol hydrochloride comprises at least the steps of:

a1) treating the L-tartrate salt, compound of formula (3).
L-tartaric acid, as defined in the fourth aspect, which
may be obtained through the process according to the
fifth aspect,

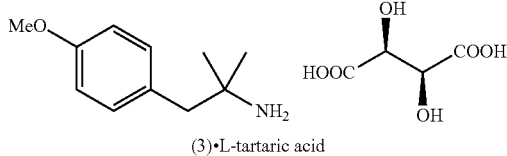

(3)·L-tartaric acid with a base in the presence of a mixture of an organic solvent and water to provide the amine of formula (3)

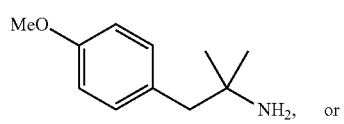

(3)

or a2) treating the maleate salt, compound of formula (3)-maleic acid, or as defined in the sixth aspect, which may be obtained through the process according to the seventh aspect,

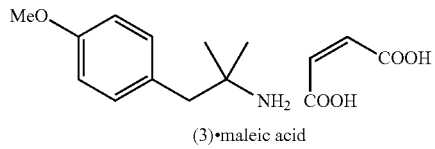

(3)·maleic acid with a base in the presence of a mixture of an organic solvent and water to provide the amine of formula (3)

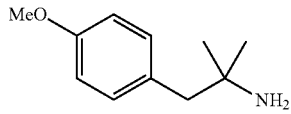

(3)

b) reacting the amine of formula (3) obtained in step a1) or a2) with epoxide of formula (2), wherein PG is a hydroxyl protecting group, in the presence of an organic solvent,

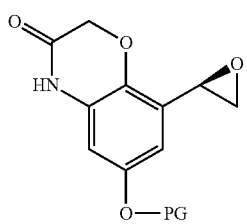

(2)

to provide the compound of formula (4)

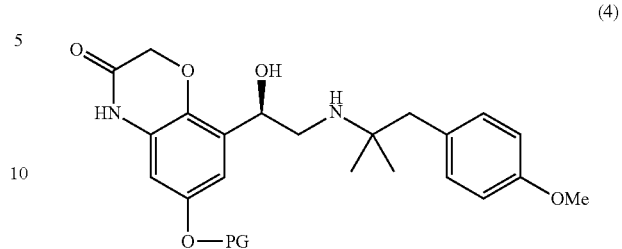

(4)

c) treating the compound of formula (4) obtained in step b) with a pharmaceutically acceptable acid HX, preferably wherein the acid HX is hydrochloric acid, camphorsulfonic, fumaric, benzoic, maleic, L-tartaric, D-tartaric, ditoluyl-L-tartaric and ditoluyl-D-tartaric, oxalic and mandelic acid, to provide compound of formula (4).HX, wherein PG is a hydroxyl protecting group as defined above

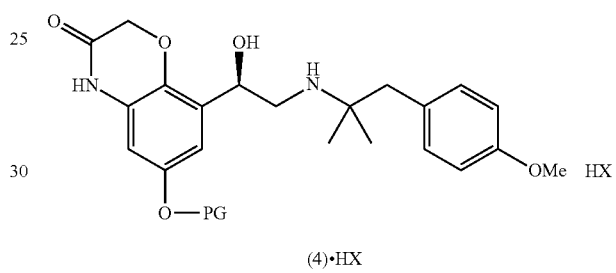

(4)·HX d) removing the hydroxyl protecting group PG from the product obtained in step c) by hydrogenation in the presence of a catalyst and an organic solvent to provide olodaterol or a pharmaceutical salt thereof, the compound of formula (1).HX, preferably olodaterol hydrochloride

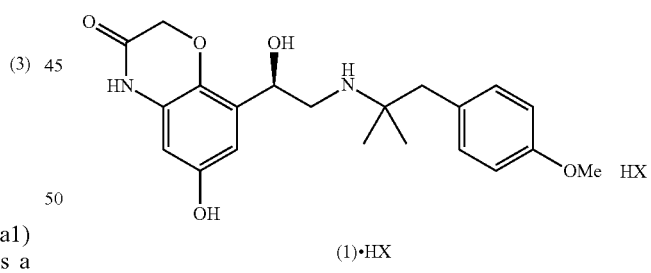

(1)·HX e) converting the pharmaceutical salt of olodaterol obtained in step d), wherein HX is not hydrochloric acid, into the hydrochloride salt of olodaterol.

In one embodiment, the process proceeds through step a1). In an alternative embodiment, the process proceeds through step a2).

A further embodiment of the third aspect of the present invention provides a process for preparing olodaterol or a pharmaceutically acceptable salt thereof, preferably the R-enantiomer of olodaterol hydrochloride, comprising at least the steps of:

a) reacting an amine of formula (3) with epoxide of formula (2), wherein PG is a hydroxyl protecting group, in the presence of an organic solvent

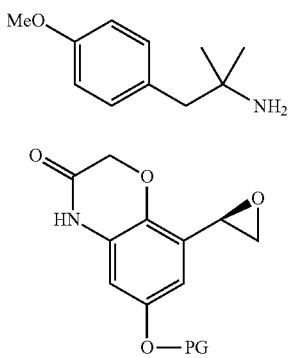

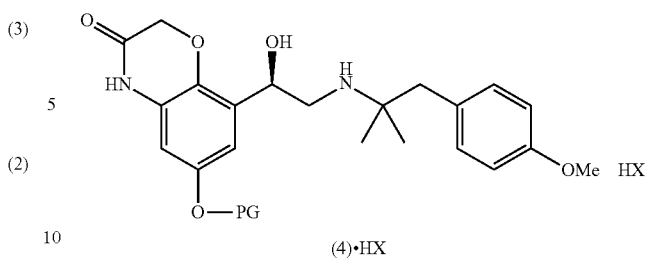

to provide the compound of formula (4)

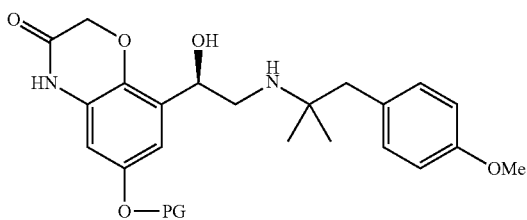

b) treating the compound of formula (4) obtained in step a) with camphorsulfonic acid, preferably the (R)-camphorsulfonic acid, to provide the camphorsulfonate salt of intermediate (4), wherein PG is a hydroxyl protecting group as defined above,

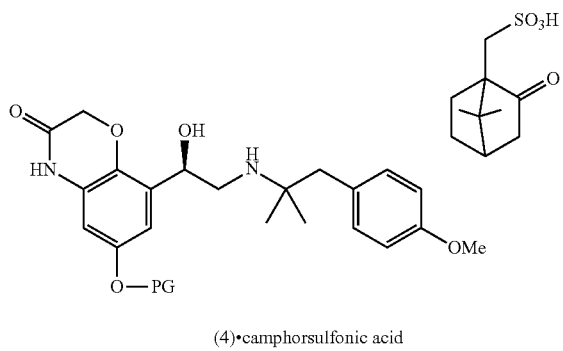

(4)•camphorsulfonic acid c) optionally treating the camphorsulfonate salt of compound (4) with hydrochloric acid, to provide compound of formula (4).HX, wherein HX is hydrochloric acid, d) removing the hydroxyl protecting group PG from the products obtained in step b) or c), by hydrogenation in the presence of a catalyst and an organic solvent to provide olodaterol or a pharmaceutical salt thereof, preferably the R-enantiomer of olodaterol hydrochloride, and e) optionally, treating olodaterol obtained in step d) with a pharmaceutically acceptable acid to provide a pharmaceutically acceptable salt thereof, preferably the R-enantiomer of olodaterol hydrochloride.

Particularly, the camphorsulfonic acid, preferably the (R)-camphorsulfonic acid, is advantageous for the purification of advanced intermediate (4) from impurities IMP-1, IMP-2, IMP-3 and IMP-4, and thus, to provide final olodaterol or salt thereof, preferably the R-enantiomer of olodaterol hydrochloride, in high chemical and enantiomeric purity.

The amine compound (3) may be obtained according to any one of the processes described above.

In the process described above, preferably PG is benzyl.

Step b) is preferably carried out as described in the second aspect of the present invention.

Step c) is optional. Thus, in one embodiment step c) is carried out. In an alternative embodiment step c) is not carried out. This step involves treating the camphorsulfonate salt of compound (4), wherein PG is a hydroxyl protecting group as defined above, with hydrochloric acid (i.e. HX is hydrochloric acid). In a particular embodiment, the camphorsulfonate salt of intermediate (4) is converted into the free base (i.e. compound (4)), for example by treatment with a suitable base such as aqueous sodium hydroxide, preferably in the presence of a suitable organic solvent as previously defined, such as an ester, preferably ethyl acetate. Compound (4) free base is then converted into the hydrochloride salt by treatment with hydrochloric acid (i.e. HX is hydrochloric acid), preferably in the presence of a suitable organic solvent as previously defined, such as an ester, preferably ethyl acetate. More preferably, the hydrochloride salt is isolated, for example by filtration optionally followed by washing (such as washing with an ester, preferably ethyl acetate).

Steps d) and e) may be carried out as previously described herein.

In a still further preferred embodiment of the third aspect of the present invention provides a process for preparing the R-enantiomer of olodaterol hydrochloride, comprising at least the steps of:

a) reacting an amine of formula (3) with epoxide of formula (2), wherein PG is a hydroxyl protecting group, in the presence of an organic solvent

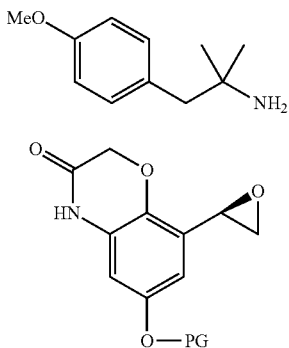

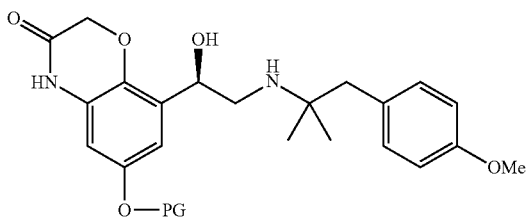

to provide the compound of formula (4)

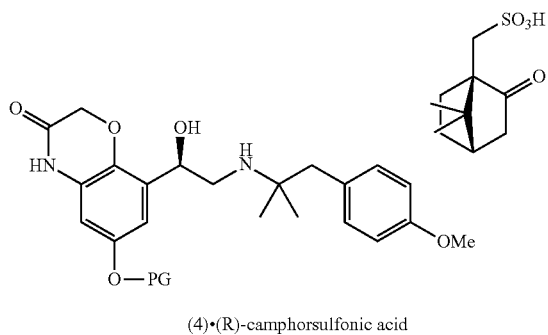

b) treating the compound of formula (4) obtained in step a) with (R)-camphorsulfonic acid, to provide the (R)-camphorsulfonate salt of intermediate (4), wherein PG is a hydroxyl protecting group as defined above,

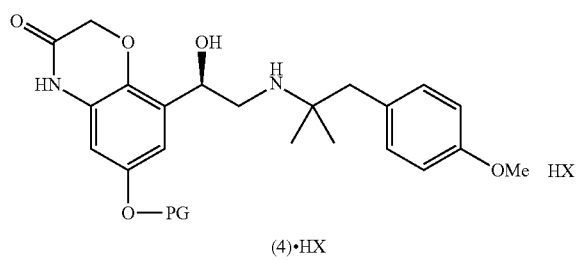

(4)·(R)-camphorsulfonic acid c) treating the (R)-camphorsulfonate salt of compound (4) with hydrochloric acid, to provide compound of formula (4).HX, wherein PG is a hydroxyl protecting group as defined above and HX is hydrochloric acid, d) removing the hydroxyl protecting group PG from the product obtained in step c), by hydrogenation in the presence of a catalyst and an organic solvent to provide the R-enantiomer of olodaterol hydrochloride The amine compound (3) may be obtained according to any one of the processes described above.

In the process described above, preferably PG is benzyl. Steps a), b) c) and d) may be carried out as previously described herein.

A further aspect of the present invention relates to the use of 1,1-dimethyl-2-(4-methoxyphenyl)ethyl amine L-tartrate salt as defined in the fourth and fifth aspects for preparing olodaterol or a pharmaceutically acceptable salt thereof, preferably the R-enantiomer of olodaterol hydrochloride.

A further aspect of the present invention relates to the use of 1,1-dimethyl-2-(4-methoxyphenyl)ethyl amine maleate salt as defined in the sixth and seventh aspects for preparing olodaterol or a pharmaceutically acceptable salt thereof, preferably the R-enantiomer of olodaterol hydrochloride.

A further aspect of the present invention relates to the use of the camphorsulfonate salt of intermediate (4) as defined in the first and second aspects for preparing olodaterol or a pharmaceutically acceptable salt thereof, preferably the R-enantiomer of olodaterol hydrochloride.

In the following, the present invention is further illustrated by examples. They should in no case be interpreted as a limitation of the scope of the invention as defined in the claims.

EXPERIMENTAL

General Methods

Proton Nuclear Magnetic Resonance ($^1$H NMR) analyses were recorded in a deuterated solvent (d6-DMSO) in a Varian Gemini 200 Fourier-Transform (FT) NMR spectrometer and chemical shifts are given in part per million (ppm) downfield from the solvent residual peak as internal standard. The coupling constants are given in Hz. Spectra were acquired dissolving 5-10 mg of sample in 0.7 mL of deuterated solvent.

Differential Scanning Calorimetry (DSC) analyses were recorded in a Mettler Toledo DSC822e calorimeter. Experimental conditions: 40 μL aluminium crucibles; atmosphere of dry nitrogen at 50 mL/min flow rate; heating rate of 10° C./min between 30 and 300° C. Data collection and evaluation was done with software STARe.

Thermogravimetric analyses (TG) were recorded in a Mettler Toledo SDTA851e thermobalance. Experimental conditions: 40 μL aluminium crucibles; atmosphere of dry nitrogen at 80 mL/min flow rate; heating rate of 10° C./min between 30 and 300° C. Data collection and evaluation was done with software STARe.

Infrared spectrometry (IR) analyses were recorded in a Perkin Elmer FT-IR spectrum One appliance using a Perkin Elmer ATR accessory.

Karl Fischer (KF) analyses were performed in a Metrohm 701 KF Titrino, equipped with an electrode Metrohm 6.0338.100 and 684/737 Coulometer (cell with diaphragm), using as reactive AQUAMETRIC Composite 5.

EXAMPLES

Example 1. 1,1-dimethyl-2-(4-methoxyphenyl)ethyl Amine Hydrochloride

To a suspension of 4-(2-methyl-2-nitropropyl)phenol (50.0 g, 256.1 mmol), $K_2CO_3$ (38.9 g, 281.7 mmol, 1.1 equiv) in acetone (200 mL) at room temperature is cautiously added dropwise dimethyl sulfate (26.7 mL, 35.5 g, 281.7 mmol, 1.1 equiv) under inert atmosphere. The resulting mixture was stirred at 58° C. for 4 hours under inert atmosphere and cooled down to room temperature. An aqueous 1M solution of NaOH (120 mL) was added and the resulting mixture was stirred for 90 min at room temperature. Then, toluene (150 mL) was added and the phases were separated. The aqueous phase was extracted with toluene and the organic phases were joined and washed with water. The solvent of the organic phase was distilled off under reduced pressure at a maximum temperature of 45° C. Afterwards, ethanol (150 mL) was added and distilled off at a maximum temperature of 45° C. The brown oil obtained was mixed with ethanol (400 mL) and hydrogenated at 15 atm of hydrogen pressure with Raney Ni (10.0 g) at 50° C. for 5 hours. The resulting mixture was filtered through a celite pad and washed with ethanol. The filtrate was distilled off under reduced pressure at a maximum temperature of 45° C. Then, ethyl acetate (250 mL) was added and partially distilled off under atmospheric pressure. Then, the resulting mixture was cooled down to 70° C. and a solution 4 M of hydrochloric acid in ethyl acetate (71.5 mL) was added for 5 min. The resulting mixture was cooled down to room temperature for 2 hours and stirred further for 2 hours. The white solid obtained was filtered off and washed with ethyl acetate.

Yield: 41.3 g (72%)

KF: 3.7-4%

DSC (10° C./min): First broad endothermic peak with onset at 86° C., due to evaporation of water, second sharp endothermic peak with onset at 170° C., due to melting.

TG (10° C./min): Weight loss of 3.9% by weight from 30° C. to 100° C. due to evaporation of water and additional weight loss starting at 180° C. due to decomposition.

Purity (HPLC): 98.0%. Significant impurities: 0.05% (compound A), 1.03% (compound B), 0.84% (compound C not characterized).

Test Example 1. Purification Effect of 1,1-dimethyl-2-(4-methoxyphenyl)ethyl Amine Hydrochloride The hydrochloride salt obtained from example 1 was treated with various solvents in order to reject the presence of significant impurities (compounds A and B). The results obtained are gathered in the table below, which demonstrate the poor effect of purification of the hydrochloride salt of 1,1-dimethyl-2-(4-methoxyphenyl)ethyl amine.

| Entry | Solvent | Type | Purity (HPLC) | Significant impurities | | |
|---|---|---|---|---|---|---|
| | | | | A | B | C |
| 1 | Solid of example 1 | N.A. | 98.0% | 0.05% | 1.03% | 0.84% |
| 2 | Acetone | Slurry | 99.4% | N.D | 0.23% | 0.26% |
| 3 | Methyl ethyl ketone | Solution | 98.0% | 0.04% | 0.98% | 0.75% |
| 4 | Ethyl acetate | Slurry | 98.0% | 0.05% | 0.99% | 0.79% |
| 5 | Isopropanol | Solution | 98.5% | N.D | 0.88% | 0.62% |
| 6 | Acetonitrile | Solution | 98.2% | N.D | 0.96% | 0.83% |
| 7 | Acetone and water (10:0.2) | Solution | 98.9% | N.D | 0.73% | 0.38% |

N.A.: Not applicable.
N.D.: Not detected.
Impurity C was not characterized.

General slurry procedure: 1,1-dimethyl-2-(4-methoxyphenyl)ethyl amine hydrochloride (5.0 g) was suspended in 50 ml of solvent, heated at the reflux temperature of the solvent and stirred for 45 min. Then, the resulting suspension was cooled down to room temperature and stirred for 2 hours. The solid obtained was filtered off, washed with solvent and dried at 45° C. under atmospheric pressure.

General crystallization procedure: 1,1-dimethyl-2-(4-methoxyphenyl)ethyl amine hydrochloride (5.0 g) was dissolved in the minimum quantity of solvent and heated at the reflux temperature of the solvent until a solution was obtained. Then, the resulting solution was cooled down to room temperature and stirred for 2 hours. The resulting solid was filtered off, washed with solvent and dried at 45° C. under atmospheric pressure.

Example 2. 1,1-dimethyl-2-(4-methoxyphenyl)ethyl Amine L-Tartrate

To a suspension of 4-(2-methyl-2-nitropropyl)phenol (10.0 g, 51.2 mmol), $K_2CO_3$ (7.8 g, 56.3 mmol, 1.1 equiv) in acetone (40 mL) at room temperature is cautiously added dropwise dimethyl sulfate (5.3 mL, 7.1 g, 56.3 mmol, 1.1 eq) under inert atmosphere. The resulting mixture was stirred at 58° C. for 4 hours under inert atmosphere and cooled to room temperature. An aqueous 1M solution of NaOH (24 mL) was added and the resulting mixture was stirred for 90 min at room temperature. Then, toluene (30 mL) was added and the phases were separated. The aqueous phase was extracted with toluene and the organic phases were joined and washed with water. The solvent of the organic phase was distilled off under reduced pressure at a maximum temperature of 45° C. Afterwards, ethanol (30 mL) was added and distilled off at a maximum temperature of 45° C. The brown oil obtained was mixed with ethanol (80 mL) and hydrogenated at 15 atm of hydrogen pressure with Raney Ni (2.0 g), at 50° C. and for 5 hours. The resulting suspension was filtered through a celite pad, washed with ethanol and distilled off under reduced pressure at a maximum temperature of 45° C. Then, the obtained brownish oil was dissolved in ethanol (50 mL) at 50° C. and a solution of L-tartaric acid (7.7 g, 1.0 equiv) in water (10 mL) was added dropwise. The resulting white suspension was stirred at 40-45° C. for 1 hour, cooled down to room temperature for 1 hour and further stirred for 1 hour. The crystals obtained were filtered off and washed with a mixture of ethanol and water (5:1; v/v).

Yield: 14.0 g (83%)

KF: 0.5%

Purity (HPLC): 98.8%. Significant impurities: 0.14% (compound A), 0.11% (compound B), 0.04% (compound C not characterized).

Example 3. Recrystallization of 1,1-dimethyl-2-(4-methoxyphenyl)ethyl Amine L-Tartrate 1,1-dimethyl-2-(4-methoxyphenyl)ethyl amine L-tartrate obtained in example 2 (1 g) was suspended in ethanol (5 mL) and heated at reflux temperature. Then, water (2 mL) was added dropwise maintaining the reflux temperature. The resulting solution was seeded, cooled to room temperature for 1 hour and further stirred for 1 hour and, finally, cooled down to 0-5° C. for 1 hour. The resulting suspension was filtered and washed with a cold mixture of ethanol and water (5:2; v/v) to give the 1,1-dimethyl-2-(4-methoxyphenyl)ethyl amine L-tartrate as an off-white solid.

Yield: 0.9 g (90%)
Purity (HPLC): 99.5%. Significant impurities: 0.02% (compound A), 0.03% (compound B).
DSC (10° C./min): Sharp endothermic peak with onset at 209-211° C.
TG (10° C./min): Weight loss starting at 180-190° C. due to decomposition.
$^1$H-NMR (200 MHz, d6-DMSO): δ/ppm 8.00-7.00 (s, 6H, NH, OH), 7.14 (d, J 10 Hz, 2H, aromatic H), 6.90 (d, J 10 Hz, 2H, aromatic H), 3.96 (s, 2H, C$\underline{H}$OH), 3.73 (s, 3H, OCH$_3$), 2.78 (s, 2H, CH$_2$), 1.17 (s, 6H, 2 CH$_3$).

Example 4. Preparation of (R)-6-(benzyloxy)-8-[1-hydroxy-2-[2-(4-methoxyphenyl)-1,1-dimethylethylamino]ethyl]-4H-benzo[1,4,]oxazin-3-one Hydrochloride 1,1-dimethyl-2-(4-methoxyphenyl)ethyl amine L-tartrate salt (1.66 g, 5 mmol) obtained from example 3 was partitioned between toluene (10 mL) and an aqueous 1M solution of NaOH (11 mL, 2.2 equiv). The aqueous phase was extracted with toluene and the organic phases obtained were joined and washed with water. The solvent of the organic phase was distilled off under reduced pressure to give 1,1-dimethyl-2-(4-methoxyphenyl)ethyl amine as a brownish oil. Then, (R)-6-benzyloxy-8-oxiranyl-4H-benzo[1,4]oxazin-3-one (1.0 g, 3.4 mmol) and 1,4-dioxane (10 mL) were added and the resulting mixture was heated at 97° C. for 17 hours. Afterwards, the mixture was cooled down to room temperature and the solvent was distilled off under reduced pressure. Then, 1,4-dioxane (2 mL) and ethanol (10 mL) were added to the resulting residue and an aqueous solution of hydrochloric acid 37% w/v (410 μL, 1.4 equiv) was added dropwise. The resulting mixture was stirred at room temperature for 2 hours, filtered, washed with ethanol and dried at 40-50° C. under atmospheric pressure.

Yield: 85-90%
Purity (HPLC): 95.0-99.9%
Enantiomeric purity (chiral HPLC): 97.0-99.9%

Example 5. Preparation of (R)-6-hydroxy-8-[1-hydroxy-2-[2-(4-methoxyphenyl)-1,1-dimethylethylaminoethyl]-2H-1,4-benzoxazin-3(4H)-one Hydrochloride A mixture of (R)-6-(benzyloxy)-8-[1-hydroxy-2-[2-(4-methoxyphenyl)-1,1-dimethylethylaminoethyl]-4H-benzo[1,4,]oxazin-3-one hydrochloride (600 mg, 1.2 mmol) obtained from example 4, palladium on charcoal 5% (40 mg) and methanol (40 mL) was hydrogenated at 3 atm of hydrogen pressure at 40° C. for 5 hours. The resulting suspension was filtered through a Celite pad. The filtrate was distilled off under reduced pressure and the resulting residue was recrystallized in a mixture of methanol and isopropanol. The suspension was filtered, washed with cold ethanol and dried.

Yield: 85-90%
Purity (HPLC): 95.0-99.9%
Enantiomeric purity (chiral HPLC method): 97.0-99.9%

Example 6. Purification of (R)-6-(benzyloxy)-8-[1-hydroxy-2-[2-(4-methoxyphenyl)-1,1-dimethylethylamino]ethyl]-4H-benzo[1,4,]oxazin-3-one (R)-6-(Benzyloxy)-8-[1-hydroxy-2-[2-(4-methoxyphenyl)-1,1-dimethylethylamino]ethyl]-4H-benzo[1,4,]oxazin-3-one hydrochloride (5.6 g, 10.9 mmol; 95.0% purity; 98.3% enantiomeric purity) as obtained from example 4 was stirred with ethyl acetate (50 mL) and an aqueous 1M solution of sodium hydroxide (50 mL). The aqueous phase was extracted with ethyl acetate and the organic phases obtained were joined and washed with water. The solvent of the organic phase was distilled off under reduced pressure to give a brownish oil. Ethyl acetate (25 mL) was added to the obtained oil and a suspension of (R)-(−)-10-camphorsulfonic acid (2.8 g, 12 mmol, 1.0 equiv) in ethyl acetate (5.6 mL) and THF (2.8 mL) was added. The resulting suspension was stirred at room temperature for 12 hours, filtered and washed with a mixture of ethyl acetate and THF (5:1) to give the corresponding (R)-(−)-10-camphorsulfonate salt as an off-white solid.

Yield: 6.4 g
Purity (HPLC): 99.3%. Significant impurities: 0.10% (IMP-1), 0.20% (IMP-2) and 0.50% (IMP-4). Enantiomeric purity (chiral HPLC): 100% (N.D. IMP-3)
The solid was recrystallized in a mixture of ethyl acetate and THF (13:4). Yield: 93%.
Purity (HPLC): 99.8%. Enantiomeric purity (chiral HPLC): 100%.
$^1$H-NMR (200 MHz, d6-DMSO): δ/ppm 9.21 (s, 1H), 9.03 (s, 1H), 7.93 (s, 1H), 7.31-7.26 (m, 5H, OCH$_2$Ph), 7.12 (d, J 10 Hz, 1H, aromatic H), 6.94 (d, J 4 Hz, 1H, aromatic H), 6.82 (d, J 10 Hz, 1H, aromatic H), 6.54 (d, J 4 Hz, 1H, aromatic H), 6.14 (s, 1H), 5.44 (s, 1H, C$\underline{H}$OH), 4.90 (s, 2H, OC$\underline{H}_2$Ph), 4.42 (d, J 28 Hz, 1H, COC$\underline{H}_a$H$_b$), 4.35 (d, J 28 Hz, 1H, COCH$_a\underline{H}_b$), 3.76 (s, 3H, OCH$_3$), 3.45 (d, J 16 Hz, 1H, CHOHC$\underline{H}_a$H$_b$NH), 2.92 (d, J 16 Hz, 1H, CHOHCH$_a\underline{H}_b$NH), 3.36-1.70 (m, 11H, 1.33 (s, 3H), 1.10 (s, 3H, CH$_3$), 0.83 (s, 3H, CH$_3$).
$^{13}$C-NMR (50 MHz, d6-DMSO): δ/ppm 216.65, 166.03, 158.92, 154.53, 126.95-137.05, 113.95, 107.03, 103.54, 70.53, 67.36, 64.57, 60.94, 58.66, 55.33, 42.83-48.06, 27.14, 24.86, 22.94, 22.80, 20.17, 19.98.
DSC (10° C./min): Sharp endothermic peak with onset at 163-167° C.
TG (10° C./min): Weight loss starting at 210° C. due to decomposition.
IR (cm$^{-1}$): 2955.7, 1745.4, 1702.1, 1617.9, 1513.7, 1470.4, 1369.7, 1329.5, 1250.0, 1162.2, 1051.5, 1038.3, 852.0, 746.7, 700.4.

Example 7. Preparation of purified (R)-6-(benzyloxy)-8-[1-hydroxy-2-[2-(4-methoxyphenyl)-1,1-dimethylethylamino]ethyl]-4H-benzo[1,4,]oxazin-3-one Hydrochloride The (R)-(−)-10-camphorsulfonate salt (1.4 g, 1.97 mmol) obtained from example 6 was stirred with ethyl acetate (14 mL) and an aqueous 1M solution of sodium hydroxide (5 mL). The phases were separated and the aqueous phase was extracted with ethyl acetate. The organic phases were joined and washed with brine. An aqueous 4N solution of HCl in ethyl acetate was added until the pH is 1-2. The resulting suspension was stirred at room temperature for 30 min and at 0-5° C. for further 30 min, filtered, washed with cooled ethyl acetate and dried.

Yield: 1.0 g
Purity (HPLC): 99.3%
Enantiomeric purity (chiral HPLC): 100%

Example 8. Preparation of purified (R)-6-hydroxy-8-[1-hydroxy-2-[2-(4-methoxyphenyl)-1,1-dimethyl-ethylaminoethyl]-2H-1,4-benzoxazin-3(4H)-one Hydrochloride A suspension of the hydrochloride salt (913 mg, 1.77 mmol), as obtained in example 7, and palladium on charcoal JM 452 (5%) in methanol (40 mL) was hydrogenated with $H_2$ at 3 atm of hydrogen pressure at 40° C. for 5 hours. The resulting suspension was filtered through a Celite pad. The filtrate was distilled off under reduced pressure and the resulting residue was recrystallized in a mixture of methanol and isopropanol. The suspension was filtered, washed with cold ethanol and dried.

Yield: 85-90%
Purity (HPLC): 99.0-99.9%
Enantiomeric purity (chiral HPLC method): 99.0-100%

Example 9. Preparation of 1,1-dimethyl-2-(4-methoxyphenyl)ethyl Amine Maleate

To a suspension of 4-(2-methyl-2-nitropropyl)phenol 100 g, 512 mmol), $K_2CO_3$ (77.8 g, 563 mmol, 1.1 equiv) in acetone (300 mL) at room temperature was cautiously added dropwise dimethyl sulfate (53.3 mL, 562 mmol, 1.1 equiv) under inert atmosphere. The line of addition of dimethyl sulfate was rinsed with acetone (100 mL) and added to the reaction. The resulting mixture was stirred at reflux temperature for 4 hours, and cooled down to room temperature. Then an aqueous 1M solution of NaOH (240 mL) was added, and the system was stirred for 90 minutes. Afterwards, toluene (300 mL) was added and phases were separated. The aqueous phase was extracted with toluene and the organic phases were joined and washed with water. The brownish oil (97.8% purity) obtained was solved in ethanol (800 mL). A half of the solution was hydrogenated at 15 atm of hydrogen pressure with Raney Ni (10.0 g) at 50° C. for 12 hours. The resulting mixture was filtered through a celite pad and a ⅓ of the solution was used and distilled off. The brownish oil obtained was mixed with maleic acid (9.9 g, 85.3 mmol, 1.0 equiv) and ethyl acetate (113 mL). The resulting suspension was heated to 50° C. and stirred until solution was obtained, and cooled down room temperature for 12 hours. The solid obtained was filtered and washed with ethyl acetate.

Yield: 17.5 g (74%)
Purity (HPLC): 99.2%. Significant impurities: 0.04% (compound A), N.D. (compound B), N.D. (compound C not characterized).

1H-NMR (200 MHz, d6-DMSO), δ/ppm 7.78 (s broad, 3H, NH, OH), 7.14 (d, J 8 Hz, 2H, H aromatic), 6.92 (d, J 8 Hz, 2H, aromatic), 6.03 (s, 2H, CH=COOH), 3.74 (s, 3H, $OCH_3$), 2.76 (s, 2H, $CH_2Ph$), 1.18 (s, 6H, 2 $CH_3$).

DSC (10° C./min): Sharp endothermic peak with onset at 96-99° C.
TG (10° C./min): Weight loss starting at 130° C. due to decomposition.

Example 10. Preparation of 1,1-dimethyl-2-(4-methoxyphenyl)ethyl Amine Hemimaleate The second half of the solution obtained in example 9 was hydrogenated at 15 atm of hydrogen pressure with Raney Ni (10.0 g) at 50° C. for 12 hours. The resulting mixture was filtered through a celite pad and a ½ of the solution was distilled off. The brownish oil obtained was mixed with maleic acid (7.4 g, 63.8 mmol, 0.5 equiv) and ethyl acetate (125 mL). The resulting suspension was heated to 50° C. and stirred until solution was obtained, and cooled down room temperature for 2 hours. The solid obtained was filtered and washed with ethyl acetate.

Yield: 23 g (76%)
Purity (HPLC): 99.3% Significant impurities: 0.09% (compound A), N.D. (compound B), 0.05% (compound C not characterized).

1H-NMR (200 MHz, d6-DMSO), δ/ppm 7.11 (d, J 8 Hz, 2H, H aromatic), 6.88 (d, J 8 Hz, 2H, aromatic), 6.03 (s, 1H, CH=COOH), 4.5-4.0 (s broad, 3H, NH, OH), 3.73 (s, 3H, $OCH_3$), 2.63 (s, 2H, $CH_2Ph$), 1.07 (s, 6H, 2 $CH_3$).

Example 11. Preparation of 4-(2-methyl-2-nitropropyl)phenol

A suspension of 4-hydroxybenzyl alcohol (1 kg, 8.06 mol), potassium hydroxide (0.23 Kg, 4.03 mol, 0.5 equiv) and tetrabutylammonium bromide (TBAB) (0.01 kg, 1% w/v) in toluene (3.0 L) was heated to 85-90° C. for 48 hours. The resulting mixture was cooled down to room temperature and an aqueous 1 N solution of HCl was added until a pH of 6-7 was observed. The solvent was distilled off. Then, ethyl acetate and water was added to the resulting residue and phases were separated. The aqueous phase was extracted with ethyl acetate and the organic phases were joined and washed with water. The organic phases were distilled off to provide 4-(2-methyl-2-nitropropyl)phenol as a brown solid, which was recrystallized in a mixture of ethyl acetate and methylcyclohexane.

Yield: 1.42 g (78%)
Purity (HPLC): 97.0-98.0%

Example 12. Preparation of (R)-6-(benzyloxy)-8-[1-hydroxy-2-[2-(4-methoxyphenyl)-1,1-dimethylethyl-amino]ethyl]-4H-benzo[1,4,]oxazin-3-one (R)-camphorsulfonate 1,1-dimethyl-2-(4-methoxyphenyl)ethyl amine L-tartrate salt (4.9 g, 14.9 mmol) was partitioned between toluene (50 mL) and an aqueous 1M solution of NaOH (50 mL). The aqueous phase was extracted with toluene and the organic phases obtained were joined and washed with water and brine. The solvent of the organic phase was distilled off under reduced pressure to give 1,1-dimethyl-2-(4-methoxyphenyl)ethyl amine as a brownish oil. Then, (R)-6-benzyloxy-8-oxiranyl-4H-benzo[1,4]oxazin-3-one (3.4 g, 11.4 mmol) and 1,4-dioxane (20 mL) were added and the resulting mixture was heated at 97° C. for 16 hours under inert atmosphere. Afterwards, the mixture was cooled down to room temperature and the solvent was distilled off under reduced pressure to provide a residue. Then, ethyl acetate (47 mL) and a solution of (R)-camphorsulfonic acid (3.4 g, 15.0 mmol) in tetrahydrofuran (28 mL) were added. The resulting solution was seeded, stirred at room temperature, filtered, washed with a mixture of ethyl acetate and tetrahydrofuran (5:1) and dried.

Yield: 4.0 g (48%)
Purity (HPLC): 99.5%
Enantiomeric purity (chiral HPLC): 99.9%

The invention claimed is:

1. A camphorsulfonate salt of intermediate (4), wherein PG is a hydroxyl protecting group selected from aralkyl groups, and wherein molar ratio of intermediate (4) to camphorsulfonic acid is 1:1

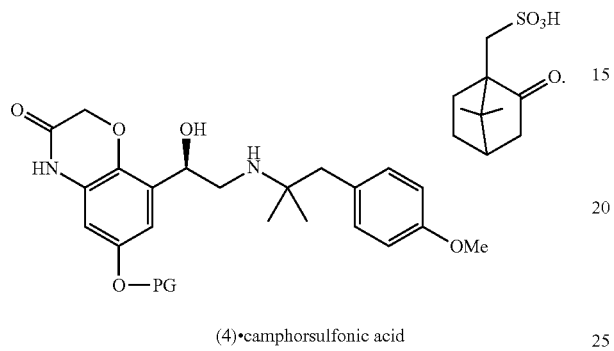

(4)·camphorsulfonic acid

2. The camphorsulfonate salt according to claim 1, of (R)-(−)-camphorsulfonic acid.

3. The camphorsulfonate salt according to claim 1, of (S)-(+)-camphorsulfonic acid.

4. The camphorsulfonate salt according to claim 1, wherein the hydroxyl protecting group is an aralkyl group selected from a) $C_1$-$C_{10}$ alkyl substituted by a $C_6$-$C_{10}$ aryl group, and b) benzyl, or p-methoxybenzyl.

5. The camphorsulfonate salt according to claim 1, wherein the hydroxyl protecting group PG is benzyl.

6. The camphorsulfonate salt according to claim 1, which is in crystalline solid form.

7. A crystalline solid form of the camphorsulfonate salt according to claim 6, characterized by at least one of the following:
    a) a DSC thermogram showing an endothermic peak with an onset at 163-166° C., or
    b) an IR spectrum showing bands at 2955, 1745, 1702, 1617, 1513, 1470, 1369, 1329, 1250, 1162, 1051, 1038, 852, 746, 700 cm$^{-1}$.

8. The camphorsulfonate salt according to claim 1, which is in non-crystalline solid form.

9. A process for preparing the camphorsulfonate salt as defined in claim 1, comprising the steps of:
    a) treating the intermediate of formula (4) wherein PG is as defined in claim 1 with camphorsulfonic acid in the presence of a solvent or a mixture of solvents

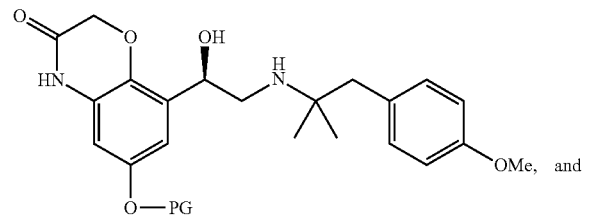

(4)

and
    b) isolating the camphorsulfonate salt obtained in step a).

10. A process for the manufacture of olodaterol or a pharmaceutical salt thereof, comprising the steps of:
    a) providing the camphorsulfonate salt of intermediate (4) as defined in claim 1;
    b) optionally treating the camphorsulfonate salt of intermediate (4) with hydrochloric acid, to provide a compound of formula (4).HX, wherein HX is hydrochloric acid

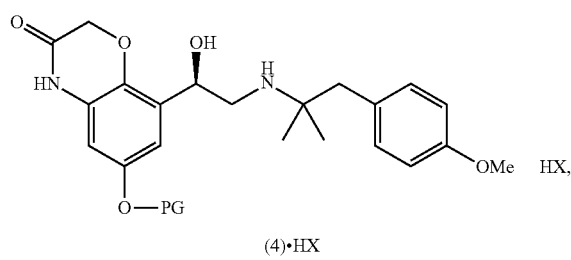

(4)·HX c) removing the hydroxyl protecting group PG from the products of steps a) or b), by hydrogenation in the presence of a catalyst and an organic solvent to provide olodaterol or a pharmaceutical salt thereof, and
    d) optionally, treating olodaterol obtained in step (c) with a pharmaceutically acceptable acid to provide a pharmaceutically acceptable salt thereof.

11. The process according to claim 10, wherein the camphorsulfonate salt of intermediate (4) is obtained by a process comprising the steps of:
    a) reacting an amine of formula (3) or a salt thereof with an epoxide of formula (2), wherein PG is a hydroxyl protecting group, in the presence of an organic solvent

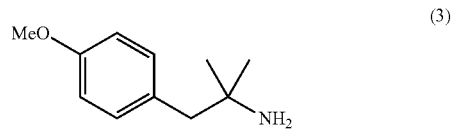

(3)

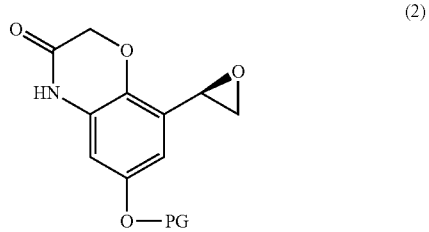

(2)

to provide the intermediate (4)

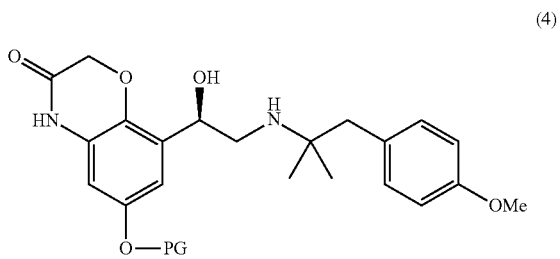

(4)

b) treating the intermediate (4) obtained in step a) with camphorsulfonic acid in the presence of a solvent or a mixture of solvents.

12. The camphorsulfonate salt according to claim 1, wherein PG is an aralkyl group selected from a) $C_1$-$C_{10}$ alkyl substituted by a $C_6$-$C_{10}$ aryl group, and b) benzyl, or p-methoxybenzyl, and wherein the camphorsulfonate salt is in crystalline solid form.

13. The camphorsulfonate salt according to claim 1, wherein PG is $C_1$-$C_{10}$alkyl substituted by a $C_6$-$C_{10}$aryl group.

14. The camphorsulfonate salt according to claim 1, wherein PG is p-methoxybenzyl.

15. The process according to claim 10, wherein step b) is carried out and comprises the additional steps of:
   b1) converting the camphorsulfonate salt of intermediate (4) into a free base in the presence of a base and a solvent, and
   b2) treating the free base with hydrochloric acid, to provide the compound of formula (4).HX.

16. The process according to claim 10, wherein the camphorsulfonate salt of intermediate (4) in step a) is an (R)-(−)-camphorsulfonate salt.

\* \* \* \* \*

UNITED STATES PATENT AND TRADEMARK OFFICE
CERTIFICATE OF CORRECTION

PATENT NO. : 10,800,748 B2  
APPLICATION NO. : 16/465762  
DATED : October 13, 2020  
INVENTOR(S) : Enric Capdevila Urbaneja Page 1 of 1

It is certified that error appears in the above-identified patent and that said Letters Patent is hereby corrected as shown below:

On the Title Page

Item (30), under Foreign Application Priority Data:  
"(EP) ...............16382628" should be -- (EP) ....................16382628.2 --.  
"(EP) ...............17382449" should be -- (EP) ....................17382449.1 --.

Signed and Sealed this  
Twenty-fourth Day of November, 2020

Andrei Iancu  
*Director of the United States Patent and Trademark Office*